US012798869B2

(12) United States Patent
Weisman et al.

(10) Patent No.: US 12,798,869 B2
(45) Date of Patent: Nov. 17, 2026

(54) ABSORBENT ARTICLE PACKAGES

(71) Applicant: The Procter & Gamble Company, Cincinnati, OH (US)

(72) Inventors: Paul Thomas Weisman, Cincinnati, OH (US); Michael Remus, Heidelberg (DE); Michael Scott Prodoehl, West Chester, OH (US); Silke Basendowski, Hofheim am Taunus (DE)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 0 days.

(21) Appl. No.: 18/794,095

(22) Filed: Aug. 5, 2024

(65) Prior Publication Data

US 2025/0058961 A1 Feb. 20, 2025

Related U.S. Application Data

(60) Provisional application No. 63/519,579, filed on Aug. 15, 2023.

(51) Int. Cl.

| | |
|---|---|
| ***B65D 85/07*** | (2017.01) |
| ***A61F 13/551*** | (2006.01) |
| ***A61F 13/84*** | (2006.01) |

(52) U.S. Cl.

CPC ............ *B65D 85/07* (2018.01); *A61F 13/551* (2013.01); *A61F 13/84* (2013.01); *A61F 2013/8497* (2013.01); *B65D 2203/02* (2013.01)

(58) Field of Classification Search

CPC ............. B65D 6/46; B65D 6/466; B65D 6/85
USPC .............................. 206/438, 440, 459.5, 494
See application file for complete search history.

(56) References Cited

U.S. PATENT DOCUMENTS

| | | | | |
|---|---|---|---|---|
| 5,655,843 | A * | 8/1997 | Conrad | B65D 75/58 206/494 |
| 6,454,095 | B1 * | 9/2002 | Brisebois | B65D 33/004 206/440 |
| 6,708,823 | B2 | 3/2004 | Cottingham et al. | |
| 7,172,073 | B2 * | 2/2007 | Hanson | B65D 5/4216 206/440 |
| 7,178,671 | B2 | 2/2007 | Nichols et al. | |
| 8,281,926 | B2 * | 10/2012 | Messerschmidt | A61F 15/001 206/439 |
| 8,479,920 | B2 * | 7/2013 | Biber | A61F 13/55105 206/459.5 |
| 8,622,618 | B2 | 1/2014 | Moehlenbrock | |
| 10,786,404 | B2 * | 9/2020 | Cheng | B65D 85/07 |
| 11,794,976 | B2 * | 10/2023 | Remus | B65D 85/07 |

(Continued)

FOREIGN PATENT DOCUMENTS

| | | | |
|---|---|---|---|
| JP | 2011184076 | A * | 9/2011 |
| WO | 2022026783 | A1 | 2/2022 |

OTHER PUBLICATIONS

Body for Absorbent Article (Year: 2011).*

(Continued)

*Primary Examiner* — Bryon P Gehman
(74) *Attorney, Agent, or Firm* — Amanda Herman Berghauer

(57) ABSTRACT

A package of one or more compressed absorbent articles with a tactile indicium is disclosed. The package encloses one or more compressed absorbent articles. The package comprises a plurality of panels forming an outer surface. The outer surface comprises a tactile indicium.

19 Claims, 23 Drawing Sheets

(56) References Cited

U.S. PATENT DOCUMENTS

| | | | | |
|---|---|---|---|---|
| 12,076,221 | B2 | 9/2024 | Remus | |
| 12,178,692 | B2 * | 12/2024 | Remus | B65D 65/466 |
| 2003/0115837 | A1 | 6/2003 | Zimmer et al. | |
| 2003/0118255 | A1 | 6/2003 | Miller | |
| 2010/0055407 | A1 * | 3/2010 | Belelie | C09D 11/34 428/172 |
| 2013/0098793 | A1 | 4/2013 | Noguchi et al. | |
| 2013/0308883 | A1 | 11/2013 | Wehrmann | |
| 2017/0057721 | A1 | 3/2017 | Lee et al. | |
| 2022/0402674 | A1 | 12/2022 | Cheng et al. | |
| 2025/0041134 | A1 | 2/2025 | Remus | |

OTHER PUBLICATIONS

PCT Search report and Written opinion for PCT/US2024/040908 dated Dec. 2, 2024, 10 pages.

All Office Actions; U.S. Appl. No. 18/792,670, filed on Aug. 2, 2024.

U.S. Appl. No. 18/792,670, filed on Aug. 2, 2024, Michael Remus.

* cited by examiner

ABSORBENT ARTICLE PACKAGES

CROSS REFERENCE TO RELATED APPLICATIONS

This application claims the benefit, under 35 U.S.C. § 119(e), to U.S. Provisional Application No. 63/519,579, filed Aug. 15, 2023, the entire disclosure of which is fully incorporated by reference herein.

FIELD

The present disclosure is directed to absorbent article packages, more particularly to absorbent article packages with a tactile indicium.

BACKGROUND

There is a constant need to make products and packages more accessible to every consumer. Different products provide different benefits and are used for different applications, while having shapes and overall appearance that may be perceived to be similar or even identical by consumers. For example, differentiation between menstrual pads, incontinence pads and liners or diapers, training pants and adult incontinence pants may only be possible due to information provided on and design of the products or packages of the products.

In particular, visual impairments create challenges when selecting and distinguishing between such different consumer products. While identifying the general type of product can be aided by shelf placement and shape of the package, consumers with impaired vision can often only differentiate between sizes, brands or specific product types, such as menstrual pads, incontinence pads and liners, by utilizing aids such as picture recognition functions of handheld devices or asking non-impaired people for help.

Non-fragile, compressible consumer products such as disposable absorbent articles (e.g., diapers and training pants, disposable adult incontinence pants and feminine hygiene pads) are often packaged and sold at retail in flexible, soft or rigid packages. Flexible packages are typically made of plastic polymer film, while rigid packages are typically made of cardboard or corrugated cardboard. Both package forms may hinder the identification of the contained product by visually impaired consumer: Rigid packages typically inhibit the perception of the product by direct touch of the human hand. Flexible packages may deform and thus identifies such as QR codes may not be readable by handheld devices.

As such, there is the need for packages aiding in using, identifying and/or differentiating consumer products with minimum visual, dexterity and cognitive skills required. Further, there is need for such packages to be produced without or with only minor adaptations and minimal negative impact on production line speeds of existing packaging lines.

SUMMARY

The present disclosure solves one or more of the problems discussed above by providing a package of one or more absorbent articles. The package encloses one or more absorbent articles. The package comprises a plurality of panels forming an outer surface. At least one of the plurality of panels comprises a package material and the package material comprises natural fibers. The outer surface comprises a tactile indicium.

Further a method of forming a tactile indicium on an outer surface of such a package is provided.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein.

DETAILED DESCRIPTION

Figure 1A:
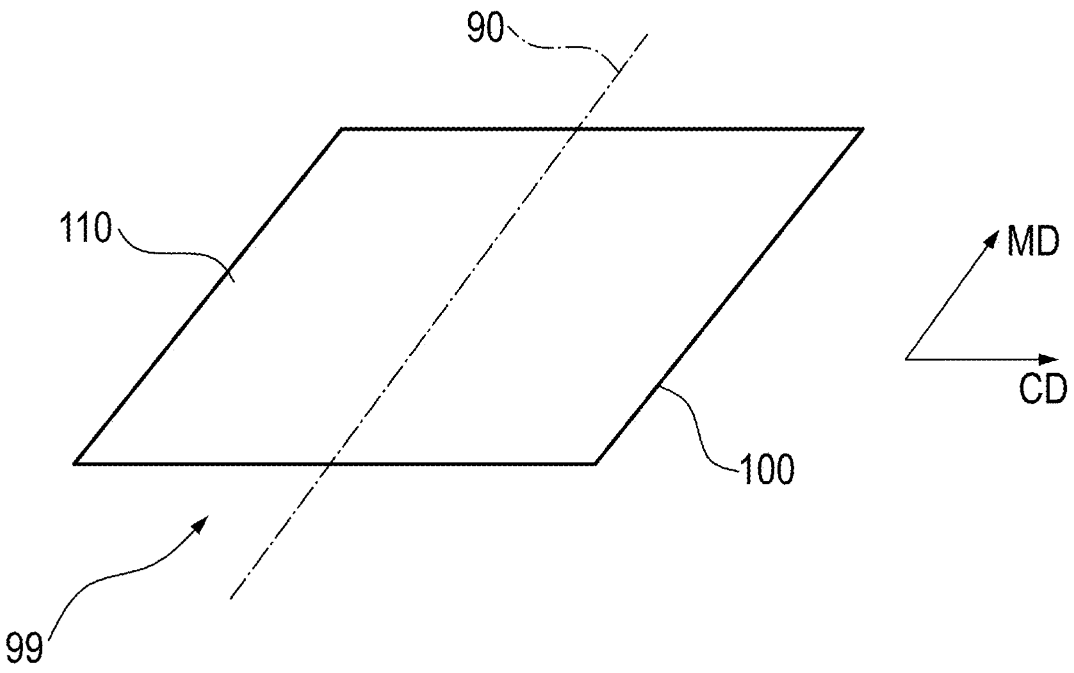
FIG. 1A is a schematic representation of a package material sheet.

The term "absorbent article", as used herein, refers to devices which absorb and contain exudates, and, more specifically, refers to devices which are placed against or in proximity to the body of the wearer to absorb and contain the various exudates discharged from the body. Absorbent articles of the present disclosure include, but are not limited to, diapers, adult incontinence briefs, training pants, diaper holders, menstrual pads, incontinence pads, liners, absorbent inserts, pantiliners, tampons, and the like.

The term "machine direction" or "MD", as used herein, refers to a path that material, such as a package material, follows through a manufacturing process.

The term "cross-machine direction" or "CD", as used herein, refers to a path that is perpendicular to the machine direction in the plane of the material.

The term "natural fibers" as used herein, refers to fibers which comprise cellulose-based fibers, bamboo fibers, and the like. Natural fibers also refers to: nonwoody fibers, such as cotton, abaca, kenaf, sabai grass, flax, esparto grass, straw, jute, hemp, bagasse, milkweed floss fibers, and pineapple leaf fibers; and woody fibers, such as wood or pulp fibers such as those obtained from deciduous and coniferous trees, including softwood fibers, such as northern and southern softwood kraft fibers, hardwood fibers, such as eucalyptus, maple, birch, and aspen. Pulp fibers may be prepared in high-yield or low-yield forms and may be pulped in any known method, including kraft, sulfite, high-yield pulping methods and other known pulping methods. The natural fibers of the present disclosure may be recycled natural fibers, virgin natural fibers or mixes thereof. Additionally, for good mechanical properties in natural fibers, it may be desirable that the natural fibers be relatively undamaged and largely unrefined or only lightly refined. The fibers may have a Canadian Standard Freeness of at least 200, more specifically at least 300, more specifically still at least 400, and most specifically at least 500.

The term "cellulose-based fibers," as used herein, may include regenerated cellulose fiber such rayon or cuprammonium rayon, and high pulping yield fibers, unless specified differently. The term "cellulose-based fibers" also includes chemically treated natural fibers, such as mercerized pulps, chemically stiffened or crosslinked fibers, or sulfonated fibers. Also included are mercerized natural fibers, regenerated natural cellulosic fibers, cellulose produced by microbes, the rayon process, cellulose dissolution and coagulation spinning processes, and other cellulosic material or cellulosic derivatives. Other cellulose-based fibers included are paper broke or recycled fibers and high yield pulp fibers. High yield pulp fibers are those fibers produced by pulping processes providing a yield of about 65% or greater, more specifically about 75% or greater, and still more specifically about 75% to about 95%. Yield is the resulting amount of processed fibers expressed as a percentage of the initial wood mass. Such pulping processes include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which leave the resulting fibers with high levels of lignin but are still considered to be natural fibers. High yield fibers are well known for their stiffness in both dry and wet states relative to typical chemically pulped fibers.

Tactile Indicium

The packages of the present disclosure comprise an outer surface comprising a tactile indicium 2. The tactile indicium 2 is perceivable by touch of the human hand, human fingers respectively, and conveys information to the consumer regarding the consumer product. The tactile indicium 2 may be a raised or indented portion of the package. For example, the tactile indicium 2 may comprise a series of raised elements, which together create a raised symbol that is perceivable by touch of the human hand and which conveys information with respect to the consumer product. Alternatively, the tactile indicium 2 may comprise a series of indented elements, which together create an indented symbol that is perceivable by touch of the human hand and which conveys information with respect to the consumer product.

The tactile indicium 2 may be an identifier for one or more property of the one or more absorbent articles. The one or more property may be selected from the group consisting of type, size and absorption capacity. The type of absorbent article may be selected from taped diapers, pant diapers, adult incontinence briefs, training pants, diaper holders, menstrual pads, incontinence pads, liners, absorbent inserts, pantiliners, tampons, and the like. In particular, the tactile indicium 2 may comprise a symbol specific to the one or more property of the one or more absorbent articles, in particular the type of absorbent article. Due to such a symbol, visually impaired consumers can readily identify absorbent articles with desired properties without utilizing any aid. In particular, such a package with symbol enables consumers to intuitively identify the desired product, even when they are not able or do not want to invest the time required to read braille text.

The tactile indicium 2 may comprise or may be braille text according to the 2010 ADA Standards for Accessible Design section 703.3. In particular, the tactile indicium 2 may be a combination of braille text according to the 2010 ADA Standards for Accessible Design section 703.3 and a symbol specific to the type of absorbent article. As such, the tactile indicium 2 is accessible to consumers not able or willing to read braille text as discussed before, while conveying extended information for consumers via the braille text.

The tactile indicium 2 may comprise a brand identifier and/or artwork. A brand identifier may exemplarily be a tradename or brand-name, either in Braille text or as elevated text, a brand logo, an icon and/or character associated with a brand or company by the consumer.

The package may comprise a printed indicium conveying the same information as the tactile indicium 2. The printed indicium may be a word, symbol, color, bar code, QR code or mixtures thereof. The printed indicium may be the same symbol as the tactile logo. Preferably, the printed indicium may be a code readable by handheld electronic devices. The printed indicium may not be raised above the base level of the outer surface or indented below the base level of the outer surface. Alternatively, the printed indicum may at least partially overlap with the tactile indicium 2.

The tactile indicium 2 may be raised above the base level of the outer surface and/or indented below the base level of the outer surface.

In one example, the printed indicum may at least partially, preferably completely, overlap with the tactile indicium 2 forming an overlapping area. The tactile logo may be raised above the base level of the outer surface, and the printed indicium may exhibit a color at the maximum height of the overlapping area. The color at maximum height of the overlapping area may be different than the color of the base level of the outer surface. Alternatively, the tactile logo may be indented below the base level of the outer surface, and the printed indicium may exhibit a color at the maximum depth of the overlapping area. The color at maximum depth of the overlapping area may be different than the color of the base level of the outer surface.

The tactile indicium 2 may comprise elements of any suitable shape. The tactile indicium 2 may comprise one or more element of square shape, rectangular shape, triangular shape, polygonal shape, (super) elliptical shape, circular shape, or a mixture thereof. The tactile indicium 2 may comprise a simple line shape element, or multiple lines shape elements. The tactile indicium 2 may comprise curved, in particular circular and/or elliptical lines and/or linear lines. The tactile indicium 2 may comprise a dot, or multiple dots. The tactile indicium 2 may comprise a mixture of lines and dots.

The tactile indicium 2 may comprise at least one tactile indicium element with a height from 50 μm to 1000 μm, preferably from 100 μm to 950 μm, more preferably from 150 μm to 900 μm, even more preferably from 200 μm to 850 μm or even from 250 μm to 800 μm according to the Tactile Height Test Method disclosed herein. All tactile indicium elements comprised by the tactile indicium 2 may have a height from 50 μm to 1000 μm, preferably from 100 μm to 950 μm, more preferably from 150 μm to 900 μm, even more preferably from 200 μm to 850 μm or even from 250 μm to 800 μm according to the Tactile Height Test Method disclosed herein. Due to this height range, the tactile indicium 2 is perceivable by touch of the hand while balancing the stress on the packaging material, in particular on flexible packaging material comprising natural fibers. Stress may lead to thinned out packaging material and thus the tactile indicium 2 collapsing or even breakage of the packaging material.

The tactile indicium 2 may comprise at least one tactile indicium element with a depth from 50 μm to 1000 μm, preferably from 100 μm to 950 μm, more preferably from 150 μm to 900 μm, even more preferably from 200 μm to 850 μm or even from 250 μm to 800 μm below the base level of the outer surface according to the Tactile Height Test Method disclosed herein. All tactile indicium elements comprised by the tactile indicium 2 may have a depth from 50 μm to 1000 μm, preferably from 100 μm to 950 μm, more preferably from 150 μm to 900 μm, even more preferably from 200 μm to 850 μm or even from 250 μm to 800 μm according to the Tactile Height Test Method disclosed herein.

The tactile indicium 2 may comprise a line or dot having a width at the base from 500 μm to 6000 μm, preferably from 750 μm to 5000 μm, more preferably from 1000 μm to 4000 μm, even more preferably from 1500 μm to 3000 μm or even from 1700 μm to 2500 μm according to the Tactile Height Test Method. Preferably, all lines and/or dots comprised by the tactile indicium 2 may have a width at the base from 500 μm to 6000 μm, preferably from 750 μm to 5000 μm, more preferably from 1000 μm to 4000 μm, even more preferably from 1500 μm to 3000 μm or even from 1700 μm to 2500 μm according to the Tactile Height Test Method. The tactile indicium 2 may comprise a line or dot having a width at half height from 300 μm to 5000 μm, preferably from 500 μm to 4000 μm, more preferably from 750 μm to 3000 μm, even more preferably from 1000 μm to 2500 μm or even from 1500 μm to 2000 μm according to the Tactile Height Test Method. Preferably, all lines and/or dots comprised by the tactile indicium 2 may have a width at half height from 300 μm to 5000 μm, preferably from 500 μm to 4000 μm, more preferably from 750 μm to 3000 μm, even more preferably from 1000 μm to 2500 μm or even from 1500 μm to 2000 μm according to the Tactile Height Test Method. Due to such width at base and/or half height an optimal balance between perceivability by touch of the hand and stability of the tactile indicium 2 can be achieved.

The tactile indicium 2 may comprise two or more tactile indicium elements of any shape. The tactile indicium 2 may comprise two or more lines or dots. The distance between any two elements comprised by the tactile indicium 2 may be from 1.0 mm to 15.0 mm, preferably from 1.5 mm to 10.0 mm, more preferably from 2.0 mm to 9.0 mm, even more preferably from 2.5 mm to 8.0 mm or even from 3.0 mm to 7.0 mm. The distance may be determined by any suitable microscopy method known in the art to the nearest 0.1 mm. By such a distance it is ensured that the individual tactile indicium elements are not perceived as one continuous element, while all elements forming one tactile indicium 2 can be identified.

The plurality of panels forming the outer surface may comprise a front panel 14, a back panel 15 opposite the front panel 14, a first side panel 12, a second side panel 13 opposite the first side panel 12, a top panel 11, and a bottom panel 10 opposite the top panel 11, wherein the panels define an interior compartment of the package 1, and wherein one or more compressed absorbent articles are disposed in the interior compartment. The tactile indicium 2 may be comprised by the front panel 14, the back panel 15, the first side panel 12, the second side panel 13, the top panel 11, or the bottom panel 10. In other words, tactile indicium 2 may be comprised by the part of the outer surface formed by the front panel 14, the back panel 15, the first side panel 12, the second side panel 13, the top panel 11 or the bottom panel 10. Preferably, the tactile indicium 2 may be comprised by the front panel 14, the back panel 15, and/or the top panel 11. The package may comprise two or more identical tactile indicia. The two or more identical tactile indicia may be comprised by one panel selected from the group of the front panel 14, the back panel 15, the first side panel 12, the second side panel 13, the top panel 11, and the bottom panel 10. The two or more identical tactile indicia may be comprised by two or more panels selected from the group of the front panel 14, the back panel 15, the first side panel 12, the second side panel 13, the top panel 11, and the bottom panel 10.

The tactile indicium 2 may be located in a distance of at least 3 mm, preferably at least 5 mm, more preferably at least 8 mm, even more preferably at least 10 mm or even at least 15 mm away from any edge formed between two of the plurality of panels. The package of the present disclosure may comprise one or more perforation line, line of weakness, fold line, seam, gusset, and/or handle. The tactile indicium 2 may be located in a distance of at least 3 mm, preferably at least 5 mm, more preferably at least 8 mm, even more preferably at least 10 mm or even at least 15 mm away from any perforation line, line of weakness, fold line, seam, gusset, and handle comprised by the package 1.

The tactile indicium 2 may cover a surface area on the outer surface of between 100 $mm^2$ and 600 $mm^2$, preferably between 110 $mm^2$ and 550 $mm^2$. The tactile indicium 2 may cover a surface area which is from 0.1% to 10%, preferably from 0.5% to 8%, more preferably from 1% to 6% of the total area of the outer surface. The front panel 14, the back panel 15, and/or the top panel 11 may comprise one or more tactile indicium 2 and the one or more tactile indicium 2 may cover a surface area which is from 0.5% to 15%, preferably from 1.0% to 10%, more preferably from 2.0% to 8% of the total area of the outer surface formed by the respective panel.

The tactile indicium 2 may comprise an embossment pattern. In particular, the package may be a flexible packaging and the tactile indicium 2 may comprise an embossment pattern. The embossment pattern may be formed by any emboss process known to those skilled in the art such as knob-to-knob embossing or nested embossing. The embossment may be formed on the package material prior to forming the package. The package material may be fed through a nip formed between juxtaposed generally axially parallel rolls. Embossing elements on the rolls may compress and/or deform the package material. The embossment pattern may be projected outward from the package outer surface. In other words, the tactile indicium 2 may comprise an embossment pattern and the embossment pattern may be raised above the base level of the outer surface. The embossment pattern may comprise line emboss elements and/or dot emboss elements.

It was surprisingly found that the amount of dot embossments and line embossments present could be adjusted relative to the total area of the embossed outer surface to provide a product accessible to visually impaired consumers and still preferred by any type of consumer. A % surface area occupied by 'dot' element embossments and a corresponding percent surface area occupied by 'line' element embossments disposed upon the total surface area of the embossed outer surface may range from 0.0% to 1.2% 'dot' element embossments and about 5.0% to about 20.0% 'line' element embossments, more preferably from about 0.3% to about 1.0% 'dot' element embossments and about 6.0% to about 10.0% 'line' element embossments, and most preferably from about 0.45% to about 0.70% 'dot' element embossments and about 6.5% to about 7.9% 'line' element embossments. Alternatively the outer surface may have a total surface area comprising at least about 0.20% of the total surface area as 'dot' embossments and at least about 0.2% of the total surface area as 'line' embossments where the ratio of 'line' embossments to 'dot' embossments may be greater than 1.0, more preferably the ratio of 'line' embossments to 'dot' embossments may be greater than 1.5, even more preferably the ratio of 'line' embossments to 'dot' embossments may be greater than 2.0, yet more preferably the ratio of 'line' embossments to 'dot' embossments may be greater than 3.0. Alternatively, if only 'line' element embossments are present in the embossing pattern then the percent embossed surface area occupied by 'line' element embossments disposed upon the total surface are of the outer surface may range from about 5.0% to about 20.0%, more preferably from about 5.0% to about 12.0%, even more preferably from about 6.0% to about 10.0%, and most preferably ranges from about 6.5% to about 7.9%.

Package Materials

The package of the present disclosure may be flexible packages or rigid packages.

At least one of the plurality of panels comprises a package material. All panels of the plurality of panels may comprise the package material. At least one of the plurality of panels may be formed of the package material. All panels of the plurality of panels may be formed of the package material. At least one of the plurality of panels comprises a package material and forms the part of the outer surface comprising the tactile indicium 2. All panels of the plurality of panels may be formed of the package material.

It is preferred that the package materials of present disclosure comprise natural and bio-sourced materials, recyclable materials, recycled materials, and/or biodegradable materials. Non-fragile, compressible consumer products such as disposable absorbent articles (e.g., diapers and training pants, disposable adult incontinence pants and feminine hygiene pads) are typically packaged and sold at retail in flexible, soft packages formed of plastic polymer film. Such plastic polymer films may be made of polyolefin material, for example polyethylene, polypropylene or any combination. Plastic polymer films may be multi-layer films, such as laminates or coextruded films, or single layer films. Plastic may withstand the rigors of a packaging process, given plastic's ability to flex and stretch. In addition, because plastic can flex and stretch without tearing upon the application of force, opening features disposed in plastic packages, tend to form clean openings while preserving the integrity of the rest of the package. Plastic packages, however, tend not to retain their shape, and may collapse upon removal of articles.

Due to the limitations of plastic and to increase recyclability and amount of natural sourced materials, package materials comprising no plastic or reduced amounts of plastic are preferred.

The package materials of the present disclosure comprise natural fibers. The package materials of the present disclosure may comprise wood fiber and/or pulp fiber. The package materials may comprise at least 50 percent by weight natural fibers, at least 70 percent by weight natural fibers, at least 90 percent by weight natural fibers, between about 50 percent and about 100 percent by weight natural fibers, between about 65 percent and about 99 percent by weight natural fibers, or between about 75 percent and about 95 percent by weight of natural fibers, specifically reciting all values within these ranges and any ranges formed therein or thereby. In one form, the package materials may comprise 99.9% percent by weight natural fibers. Package materials comprising natural fibers may be preferred not only due to environmental reasons, but also due to the increased stability of the tactile indicium 2 in comparison to plastic-based package materials.

Inks and/or dyes associated with the package art, branding, package information, and/or background color, as well as adhesives associated with the seams and barrier coatings are also considered part of the package materials on a weight percentage basis. Where the weight percentage of natural fibers is less than 100 percent, the difference may be made up by inks, dyes, and/or adhesives. Inks, dyes, coatings, and adhesives may be considered contaminants in a paper recycling process, but may be otherwise recyclable.

While the package materials may comprise many different fibers, inks, dyes, coatings, adhesives, etc., the package material of the present disclosure may be constructed to facilitate and/or encourage recycling of the package material, and may encourage recycling of the package material within a single recycling stream, such as a paper recycling stream. Whether package materials are recyclable may vary from region to region. In order to meet one of the highest standards for recyclability, the total weight percentage of non-recyclable material, including material not recyclable within a particular recycling stream—such as a paper recycling stream—but otherwise recyclable, e.g. inks, dyes, adhesives, and coatings in the package material may be 5 percent by weight of the package material or less, or between 0.1 percent to 5 percent by weight, specifically reciting all values within these ranges and any ranges formed therein. However, other jurisdictions may allow a higher weight percentage of non-recyclable material. For example, in other jurisdictions, the package material of the present disclosure may comprise 50 percent by weight or less, 30 percent by weight or less, or about 15 percent by weight or less of non-recyclable material, specifically including all values within these ranges and any ranges formed therein or thereby. As another example, the package materials of the present disclosure may comprise from between about 0.1 percent to about 50 percent by weight, from about 0.1 percent to about 30 percent by weight, or from about 0.1 percent to about 15 percent by weight of non-recyclable material, specifically including all values within these ranges and any ranges formed therein or thereby. In an example, the amount of inks, dyes, coatings, and adhesives is 5 percent by weight, or less, or between 0.1 percent by weight to 5 percent by weight, specifically reciting all values within these ranges and any ranges formed therein.

The package materials of the present disclosure may be free of a barrier layer. As used herein, the term "barrier layer" refers to a layer of material, including barrier coatings, barrier plastics, and/or barrier foils, that is joined to the package materials comprising natural fibers. Such barrier layers may reduce the recyclability of the package materials within a single recycling stream.

In other instances, in order to at least partially protect absorbent articles disposed within the package, the package materials of the present disclosure may comprise a barrier layer. The barrier layer may at least partially inhibit the migration of water vapor through the package material. The barrier layer may comprise a water soluble material that may not interfere with a recycling process. The barrier layer may be easily separable from the remainder of the package materials through a recycling process, for example by having a different water solubility, density, buoyancy, or other physical features as compared to the remainder of the package materials.

The type of adhesives utilized for the seals of the packages of the present disclosure may impact the recyclability of the package as well. As an example, adhesives that can dissolve in water during the re-pulping step or the disintegration step of the paper recycling process may be particularly suitable for the packages of the present disclosure. Such adhesives include starch based adhesives, polyvinyl acetate based adhesives, and polyethylene oxide based adhesives. A suitable example of a starch based adhesive is available from LD Davis located in Monroe, North Carolina, under the trade name AP0420CR. A suitable example of a polyvinyl acetate based adhesive is available from Sekisui Chemical Company, located in Osaka, Japan, under the trade name Selvol 205. A suitable example of a polyethylene oxide based adhesive is available from Dow Chemicals Co. located in Midland, Michigan, under the trade name WSR N-80.

Water-dispersible adhesives may similarly be utilized. Suitable examples of water dispersible adhesives include thermoplastic elastomer based adhesives and polyvinyl acetate based adhesives. A suitable example of a thermoplastic elastomer based adhesive is available from Actega located in Blue Ash, Ohio, under the trade name Yunico 491. A suitable example of a polyvinyl acetate based adhesive is available from Bostik located in Milwaukee, Wisconsin, under the trade name Aquagrip 4419U01. Another suitable example of a polyvinyl acetate based adhesive is available from HB Fuller under the trade name PD-0330.

Without wishing to be bound by theory, it is believed that packages of the present disclosure which utilize adhesives dissolvable in water may comprise a higher weight percentage of such adhesives than adhesive which are only water dispersible. For example, packages comprising water dissolvable adhesives may comprise a first weight percentage of adhesive while packages comprising water dispersible adhesives may comprise a second weight percentage of adhesive. The first weight percentage may be greater than the second weight percentage for the purposes of recycling the package material.

Where a barrier layer is utilized, the barrier material may be selected such that the use of adhesives can be reduced or eliminated. One such barrier material may be polyethylene film coated on an inner surface of the package material. The polyethylene may be utilized to form the seals rather than an adhesive or in conjunction with an adhesive. However, as the polyethylene film may not be recyclable in the same stream as the other package materials, the weight percentage of the polyethylene may be in accordance with the present description regarding percentages of non-recyclable material discussed herein.

The higher the percent yield of natural material, the more likely the material is able to be recycled in a paper recycling stream. In order to accommodate the higher percent yield of natural material, e.g. wood pulp and/or cellulose, the weight percentage of barrier layer compared to that of the natural fiber should be substantially less. The barrier layer may comprise one or more barrier film layers. The one or more barrier film layers may be polyethylene film layers. As an example, one or more barrier film layers can make up about 40 percent by weight or less, about 30 percent by weight or less, about 20 percent by weight or less, about 10 percent by weight or less, about 5 percent by weight or less, or about 5 percent to about 20 percent, of the overall package material. As another example, one or more barrier film layers can make up from between about 3 percent by weight to about 40 percent by weight, from about 3 percent by weight to about 30 percent by weight, or from about 3 percent by weight to about 20 percent by weight. In one specific example, one or more barrier film layers may make up about 5 percent by weight or less of the overall package material weight, about 4 percent or less, or about 3 percent or less. In another specific example, the film may make up from between about 1 percent by weight to about 5 percent by weight, from about 1 percent by weight to about 4 percent by weight, or from about 1 percent by weight to about 3 percent by weight.

The one or more barrier layers or one or more barrier film layers may comprise the natural fibers being coated with clay, hectorite, and/or PET that is not sealable, but does provide a suitable barrier. Another option would be to join metalized paper, or other inorganic barrier material, to the natural fibers, which again provides a suitable barrier. Aluminiumoxide barriers or layers are also contemplated to be joined to or indirectly attached to or deposited on the natural fibers. The Aluminiumoxide barriers are transparent which may be desirable and/or less noticeable to consumers. With all of these options, bonding enhancement agents may be applied to seal and/or seam areas on the inner surface of the package material to allowed seals or seams to be formed when the package is made even though the initial barrier materials are not sealable. An example of a bonding enhancement agent is a heat sealable adhesive, a thermoplastic polymer, a hot melt polymer, water based adhesive, a coextruded polymeric layer, or combinations thereof. Bonding enhancement agents may be flexo-printed, dispersion coated, applied by ink jet printing, or applied using any other specific application technology. In general, the clay, hectorite, PET, metalized paper, inorganic barriers, and/or aluminiumoxide, including the bonding enhancement agents in the seal or seam areas may be less than about 15%, less than about 10%, less than about 5%, about 2% to about 10%, or about 3% to about 8%, by weight of the laminate of these materials and the natural fibers so as to meet recycling requirements.

The basis weight of the one or more barrier layers may be at least about 2 gsm to less than about 25 gsm. It is theorized that below this basis weight, the film may not cover a sufficient enough portion of the bag to provide a suitable barrier property. However, aside from the foregoing, the one or more barrier film layers may be any suitable basis weight so long as the one or more barrier film layers' basis weight is within the weight percentages described herein. It is worth noting that the one or more barrier film layers laminated, coated, or otherwise joined to the natural fiber layer forms a synergistic relationship particularly where the one or more barrier film layers are desired to be a smaller weight percentage of the overall package material. For example, where the one or more barrier film layers is 5 percent by weight or less of the overall package material, this can be a very small basis weight barrier film layer for the basis weight of package materials described heretofore. At this very low basis weight, it is believed that the one or more barrier film layers would not be able to be processed reliably without being coated, laminated, or otherwise joined to the natural material layer. And similarly, without the addition of the one or more barrier film layers, the natural material layer may not be able to 5 provide much, if any, inhibition to the absorption of moisture vapor by the SAP within the absorbent articles in the package.

The effectiveness of the recycling process on the package material of the present disclosure may be determined via recyclable percentage. Package material of the present disclosure may exhibit recyclable percentages of 60 percent or greater, 75 percent or greater, or 90 percent or greater, specifically reciting all values within these ranges and any ranges formed therein or thereby. The packaging material of the present disclosure may have a recyclable percentage of between about 60 percent and about 99.9 percent, between about 75 percent and about 99.9 percent, or between about 90 percent and about 99.9 percent, specifically reciting all values within these ranges and any ranges formed therein or thereby. In a specific example, the package material of the present disclosure may exhibit a recyclable percentage of between about 95 percent and about 99.9 percent, specifically including all values within these ranges and any ranges formed therein. The recyclable percentage of the package material of the present disclosure is determined via test PTS-RH:021/97 (Draft October 2019) under category II, as performed by Papiertechnische Stiftung located at Pirnaer Strasse 37, 01809 Heidenau, Germany.

Along with recyclable percentage, the total reject percentage is determined via the PTS-RH:021/97 (Draft October 2019) under category II Test Method. The total reject percentage of the package material of the present disclosure may be 40 percent or less, 30 percent or less, or 10 percent or less, specifically including all values within these ranges and any ranges formed therein or thereby. For example, the total rejection percentage of the package material of the present disclosure may be from about 0.5 percent to about 40 percent, from about 0.5 percent to about 30 percent, or from about 0.5 percent to about 10 percent, specifically reciting all values within these ranges and any ranges formed therein or thereby.

It is believed that the percent non-recyclable material does not necessarily have a 1:1 correlation to the total reject percentage. For example, dissolvable adhesives and/or coatings are designed to dissolve during the recycling process. It is theorized that these adhesive may not have an impact the total reject percentage; however, they would contribute to the non-recyclable material weight percent.

The PTS-RH:021/97 (Draft October 2019) under category II Test Method also comprises a visual component. Trained screeners inspect one or more handsheets of recycled package material for visual imperfections. If the number of visual imperfections is too great, then the package material is rejected. If the number of visual imperfections is acceptable, in accordance with the PTS-RH:021/97 (Draft October 2019) under category II Test Method, then the package material is approved for additional processing. The package material of the present disclosure may yield an acceptable level of visual imperfections during this step of the method.

The package material of the present disclosure may yield the recyclable percentages mentioned heretofore as well as pass the visual screening method. Thus, the package material of the present disclosure may achieve an overall score or final outcome of "pass" when subjected to the PTS-RH:021/97 (Draft October 2019) under category II Test Method.

It is also worth noting that there is an alternative method for determining the recyclable percentage of the package material of the present disclosure. The Test Method performed by the University of Western Michigan, called the Repulpability Test Method, may provide a percent yield of recyclable material. While there are subtle differences between the Repulpability Test Method performed by Western Michigan and the PTS-RH:021/97 (Draft October 2019) under category II Test Method, it is believed that the percentage yield of the Repulpability Test Method would be similar to the recyclable percentage provided by the PTS Test Method.

It is contemplated that the package material of the present disclosure, while being recyclable, may itself comprise recycled material. Such determination can be made from a visual inspection of the package. For example, manufacturers typically advertise the use of recycled materials in an effort to demonstrate their eco-friendly product approach. To further expand on this example, some manufacturers may utilize a logo, e.g., a leaf, along with wording to indicate the use of recycled material in the package material. Often times, manufacturers may specify the percentage of recycled material utilized as well, e.g., over 50 percent, over 70 percent, etc. Visual inspection may be as simple as utilizing the human eye to inspect packages for logos of the use of recycled material. Additionally, or alternatively, visual inspection may include microscopy methods such as optical microscopy, scanning electron microscopy or other suitable methods known in the art. For example, package material comprising recycled paper fibers may appear different under a microscope due to the presence of a much wider range of natural fiber types than if the package material comprised of 100% non-recycled paper. As another example, under a microscope, recycled fibers-due to their increased processing—may appear more fibrillated than their virgin fiber counterparts.

In order to withstand the rigors of a high speed manufacturing process where a plurality of absorbent articles are placed within the package, withstand the force of compressed absorbent articles being placed directly into the package without an intermediate package or container, withstand the rigors of being shipped, provide protection from environmental insults during shipping and while on the store shelf, and provide for product protection while in the consumers home, the package materials may have some level of strength, stretch, and/or resilience. The package materials of the present disclosure may be characterized using metrics such as: MD Tensile Strength in kN/m, CD Tensile Strength in kN/m, MD Stretch At Break in percent, CD Stretch At Break in percent, Burst Strength in kPa, Caliper in μm, MD Tensile Energy Absorption in $J/m^2$, CD Tensile Energy Absorption in $J/m^2$, and Basis Weight in grams per square meter. While all of the metrics may be utilized together to characterize the package materials of the present disclosure, it is believed that some of the metrics alone or in conjunction with others may suffice to characterize package materials which are suitable for packaging absorbent articles. As an example, it is believed that the Burst Strength may be utilized alone or in conjunction with other metrics to obtain package materials which are sufficient for packaging of absorbent articles. Similarly, it is believed that the Tensile Energy Absorption (TEA) in the MD and CD may be utilized in conjunction with one another, and if desired, along with any other combination of the above metrics, to obtain package materials which are suitable for packaging of absorbent articles. As yet another example, it is contemplated that MD Stretch At Break and/or CD Stretch At Break may be utilized in conjunction with at least one of MD Tensile Strength or CD Tensile Strength, respectively, to characterize package materials which may be sufficient to package absorbent articles as described herein. Any suitable combination of metrics may be utilized.

The package materials of the present disclosure may have an MD Tensile Strength of at least 5 kN/m, at least 7 kN/m, or at least 8 kN/m, specifically reciting all values within these ranges and any ranges formed therein or thereby. The MD Tensile Strength may be between about 5 kN/m and about 8.5 kN/m, between about 5.2 kN/m and about 8.2 kN/m, or between about 5.5 kN/m and about 8.0 kN/m, specifically reciting all values within these ranges and any ranges formed therein or thereby. The MD Tensile Strength is measured using the Strength Tensile Test Method described herein.

The package materials of the present disclosure may have a CD Tensile Strength of at least 3 kN/m, at least 4 kN/m, or at least 5.5 kN/m, specifically reciting all values within these ranges and any ranges formed therein or thereby. The CD Tensile Strength may be between about 3 kN/m and about 6.5 kN/m, between about 3 kN/m and about 6.2 kN/m, or between about 3 kN/m and about 6 kN/m, specifically reciting all values within these ranges and any ranges formed therein or thereby. The CD tensile strength is measured using the Strength Tensile Test Method.

The package materials of the present disclosure may have a Burst Strength of at least 200 kPa, at least 250 kPa, or at least 550 kPa, specifically reciting all values within these ranges and any ranges formed therein or thereby. The Burst Strength of the package materials of the present disclosure may be between about 200 kPa and about 600 kPa, between about 220 kPa and about 550 kPa, or between about 250 kPa and about 500 kPa, specifically reciting all values within these ranges and any ranges formed therein or thereby. The Burst Strength is measured using the Burst Strength Test Method described herein. It is believed that the Burst Strength, as measured, includes components of strength, flexibility, and resiliency. As such, it is believed that Burst Strength may be used independently from the other metrics mentioned.

The package materials of the present disclosure, in addition to strength, may also exhibit some measure of resiliency. Thus, the package materials of the present disclosure may exhibit an MD Stretch At Break of at least 3 percent, at least 4 percent, or at least 6 percent, specifically reciting all values within these ranges and any ranges formed therein or thereby. The package materials of the present disclosure may exhibit an MD Stretch At Break of between about 3 percent and about 6.5 percent, between about 3.2 percent and about 6.2 percent, or between about 3.5 percent and about 6 percent, specifically reciting all values within these ranges and any ranges formed therein or thereby. The MD Stretch At Break is measured using the Strength Tensile Test Method described herein.

The package materials of the present disclosure may exhibit a CD Stretch At Break of at least 4 percent, at least 6 percent, or at least 9 percent, specifically reciting all values within these ranges and any ranges formed therein or thereby. The package materials of the present disclosure may exhibit a CD Stretch At Break of from about 4 percent and about 10 percent, from about 4.5 percent and about 9.5 percent, or from about 5 percent and about 9 percent, specifically reciting all values within these ranges and any ranges formed therein or thereby. The CD Stretch At Break is measured using the Strength Tensile Test Method described herein.

Regarding Caliper, the package materials of the present disclosure may exhibit a Caliper of at least 50 μm, at least 70 μm, or at least 90 μm, specifically reciting all values within these ranges and any ranges formed therein or thereby. The package materials of the present disclosure may exhibit a Caliper of between about 50 μm and about 110 μm, from about 55 μm and about 105 μm, or from about 60 μm and about 100 μm, specifically reciting all values within these ranges and any ranges formed therein or thereby. Caliper is measured using the Caliper Test Method described herein.

Regarding Tensile Energy Absorption (TEA), the package materials of the present disclosure may exhibit an MD TEA of at least 150 $J/m^2$, greater than 170 $J/m^2$, or at least 180 $J/m^2$, specifically reciting all values within these ranges and any ranges formed therein or thereby. The package materials of the present disclosure may have an MD TEA of between about 100 $J/m^2$ and about 250 $J/m^2$, between about 125 $J/m^2$ and about 225 $J/m^2$, or between about 150 $J/m^2$ and about 200 $J/m^2$, specifically reciting all values within these ranges and any ranges formed therein or thereby.

The package materials of the present disclosure may have a CD TEA of at least 150 $J/m^2$, at least 200 $J/m^2$, or at least 250 $J/m^2$, specifically reciting all values within these ranges and any ranges formed therein or thereby. The package materials of the present disclosure may have a CD TEA of between about 150 J/m$^2$ and about 275 J/m$^2$, from about 175 J/m$^2$ and about 260 J/m$^2$, or between about 200 J/m$^2$ and about 250 J/m$^2$, specifically reciting all values within these ranges and any ranges formed therein or thereby. TEA in the MD and CD are measured according the Strength Tensile Test Method described herein.

The Basis Weight of the package materials may affect the "feel" of the package to the consumer as well as the strength of the package and the stability of the tactile indicium 2. Too low of a Basis Weight and the package may feel too flimsy. Too high and the package may feel too inflexible. The package materials of the present disclosure have a Basis Weight of between about 50 gsm and about 120 gsm, between about 55 and about 115 gsm, or between about 60 gsm and about 110 gsm, specifically reciting all values within these ranges and any ranges formed therein or thereby. The Basis Weight, also referred to as "grammage", is determined according to the Basis Weight Test Method described herein. In particular, the package materials may comprise natural fibers and may have a Basis Weight of between about 50 gsm and about 120 gsm, between about 55 and about 115 gsm, or between about 60 gsm and about 110 gsm according to the Basis Weight Test Method described herein. Moreover, the package materials may comprise at least 50 percent by weight natural fibers, at least 70 percent by weight natural fibers, at least 90 percent by weight natural fibers, between about 50 percent and about 100 percent by weight natural fibers, between about 65 percent and about 99 percent by weight natural fibers, or between about 75 percent and about 95 percent by weight of natural fibers and may have a Basis Weight of between about 50 gsm and about 120 gsm, between about 55 and about 115 gsm, or between about 60 gsm and about 110 gsm according to the Basis Weight Test Method described herein. By this, an optimal stability of the tactile indicium 2 on a flexible package, which in addition exhibits good recyclability is provided.

It is worth noting that for high speed packaging processes, the lower Basis Weight of 50 gsm may provide some quality assurance outages. It is believed that high speed packaging processes may cause strain on the packaging materials that slower packaging processes may not. Therefore, where package materials are processed using a high speed manufacturing process, 60 gsm may be the lowest desirable package material Basis Weight. Where package materials are processed using a hand packing process or lower speed packaging processes, 50 gsm may be sufficient as the lowest package material Basis Weight.

In one form, the package materials of the present disclosure may be different than carton board and cardboard. For example, carton board may not be as flexible as the preferred package materials of the present disclosure. Carton board is inherently stiffer than the flexible package materials of the present disclosure and does not have the processability on high speed converting lines as does the flexible package materials of the present disclosure. Additionally, carton board generally has a Basis Weight greater than 160 gsm, which is considerably higher than the preferred Basis Weight of the package materials of the present disclosure.

Similarly, cardboard may also be different from the package materials of the present disclosure. Cardboard has a much higher Basis Weight (greater than 200 gsm) than the preferred Basis Weight of the package materials of the present disclosure. Additionally, cardboard is much less flexible than the preferred flexible package materials of the present disclosure. Cardboard materials are commonly fluted and comprise three plies of a paper material and, as such, may be structurally different than the package materials of the present disclosure.

In some described forms, the package materials of the present disclosure may have the advantage of being more flexible as compared to carton board and cardboard. Another advantage is that the preferred package materials of the present disclosure take up less space than the more-bulky carton board and cardboard. A further advantage of the preferred package materials of the present disclosure, attributable at least in part to the strength and resiliency properties discussed herein, is that the package materials allow the packaged absorbent articles to be compressed within the package. This allows for more products to fit within a smaller volume package which may increase manufacturing efficiency. One additional advantage is that a single layer (one ply) of the package materials of the present disclosure may form packages of the present disclosure. The inventors have found that, due at least in part to the flexibility, strength, and resiliency properties of the package materials, packages of the present disclosure may be formed from a single layer (one ply) of package materials of the present disclosure.

Despite having reduced flexibility compared to, for example, plastic packaging, and lower Basis Weight than cardboard and carton board, the inventors have surprisingly found the preferred packaging materials of the present disclosure may withstand the rigors of a high speed manufacturing process—where a plurality of absorbent articles are placed within the package under compression—as well as the rigors of being shipped, provide protection from environmental insults during shipping and while on the store shelf, and provide protection for absorbent articles while in the consumers home.

Table 1 shows a variety of package materials which are able to be successfully utilized in packaging absorbent articles under high speed processing conditions, along with at least one package material which is not successful. The various properties discussed previously are also listed for each of the samples.

Sample 1: Packaging paper produced from pure, white kraft pulp and consisting entirely of virgin fibers, available from BillerudKorsnäs™ under the trade name Axello Tough White.

Sample 2: Packaging paper produced from pure, white kraft pulp and consisting entirely of virgin fibers, available from BillerudKorsnäs™ under the trade name Performance White SE.

Sample 3: Calendered specialty kraft paper consisting entirely of virgin fibers, available from Mondi™ under the trade name Advantage Smooth White Strong.

Sample 4: Packaging paper produced from kraft pulp, made of virgin fibers, and comprising a barrier coating of fluoropolymers, available from BillerudKorsnäs™ under the trade name Basix Glaze.

TABLE 1

| | Sample 1 | Sample 2 | Sample 3 | Sample 4 |
|---|---|---|---|---|
| Basis Weight (gsm) | 80 | 70 | 70 | 50 |
| MD Tensile Strength(kN/m) | 7.6 | 5.7 | 5.9 | 4.7 |
| CD Tensile Strength (kN/m) | 4.7 | 4.1 | 3.0 | 2.7 |
| Burst Strength (kPa) | 480 | — | 256 | 185 |
| MD Stretch At Break (%) | 4.5 | 6.0 | 2.5 | — |

TABLE 1-continued

| | Sample 1 | Sample 2 | Sample 3 | Sample 4 |
|---|---|---|---|---|
| CD Stretch At Break (%) | 8.0 | 9.5 | 8.0 | — |
| Caliper (μm) | 92.0 | — | 89.0 | 67.0 |
| TEA MD (J/m$^2$) | 185 | 230 | — | — |
| TEA CD (J/m$^2$) | 240 | 200 | — | — |

The package material of Sample 4 is not able to be successfully utilized in the packaging of absorbent articles. During the placement of absorbent article in the package, the package material tore. Without wishing to be bound by theory, it is believed that Sample 4 failed due to a combination of low Basis Weight and a high speed packaging process. While Sample 4 failed under the conditions of the high speed process, it is believed that a sample having the properties of Sample 4 may be successful with the use of a gentler packaging process, such as hand packing.

Package Configurations

The package materials of the present disclosure may be arranged as a package in a myriad of configurations to contain absorbent articles. For example, the package may comprise a plurality of panels which define an interior compartment and enclose one or more than one compressed absorbent article. When in a sealed state, such as during transport and on display on a store shelf, the package may completely enclose the one or more than one compressed absorbent article. Each of the panels comprises an inner surface—facing inward toward the packaged absorbent article—and an outer surface—facing outward toward the consumer. The outer surface and/or inner surface of one or more panels may comprise inks or dyes which create branding on the package, package information, and/or background color. The branding and/or package information associated with the absorbent articles within the package may be provided on an outer surface of at least one panel. Branding may include logos, trade names, trademarks, icons, and the like, associated with the absorbent articles within the package. Branding may be utilized to inform a consumer of the brand of the absorbent articles within the package. As an example, branding for a package of feminine hygiene pads may comprise the brand name Always®. Package information may include the size of the absorbent articles, the number of absorbent articles within the package, an exemplary image of the absorbent articles contained within the package, recyclability logos, and the like. As an example, package information for a package of feminine hygiene pads may comprise a size indicator, e.g., "Size 1."

In an alternative example—not encompassed by the wording of the claims—, the package 1 of the present disclosure may enclose a household care product. The household care product may comprise a detergent product, preferably a laundry care composition, a dish care composition, a hard surface care composition or a mixture thereof. Alternatively, the household product may be an air care product. The household care product may be a gas, a liquid, a powder, a unit dose article a bead, a compressed tablet, or a mixture thereof. When the household care product is a unit dose article, preferably the unit dose article comprises a water-soluble film shaped to house the laundry care composition, a dish care composition, a hard surface care composition or a mixture thereof. Alternatively, the unit dose article may be a fibrous unit dose article. The detergent composition may be a laundry detergent composition, an automatic dishwashing composition, a hard surface cleaning composition, or a combination thereof. The detergent composition may comprise a solid, a liquid, or a mixture thereof. The term liquid includes a gel, a solution, a dispersion, a paste, or a mixture thereof. The liquid may be a compressed liquid. Without wishing to be bound by theory, the tactile indicium 2 may represent a symbol that describes the intended use of the household care product and which can be detected by the touch of the human hand. As well as information regarding the intended use of the household care product, the tactile indicium 2 may provide information such as how to use the product and/or health and safety information.

The package materials of the present disclosure may be supplied by a manufacturer of package materials to an absorbent article manufacturer. The package materials may be pre-formed to some extent into a finished package shape, or the manufacturer of package materials may simply provide rolls of the package materials to the absorbent article manufacturer. The package material may be unitary, meaning that a package is formed from a single piece of package material. For example, multiple folds and seams may be utilized to form the plurality of panels of the package from a single piece of package material. In such examples, the absorbent article manufacturer may create the folds and seams as described herein to form a package for absorbent articles. The packages of the present disclosure may comprise package material which comprises a plurality of discrete portions. Such configurations are described in additional detail herein.

Figure 1B:
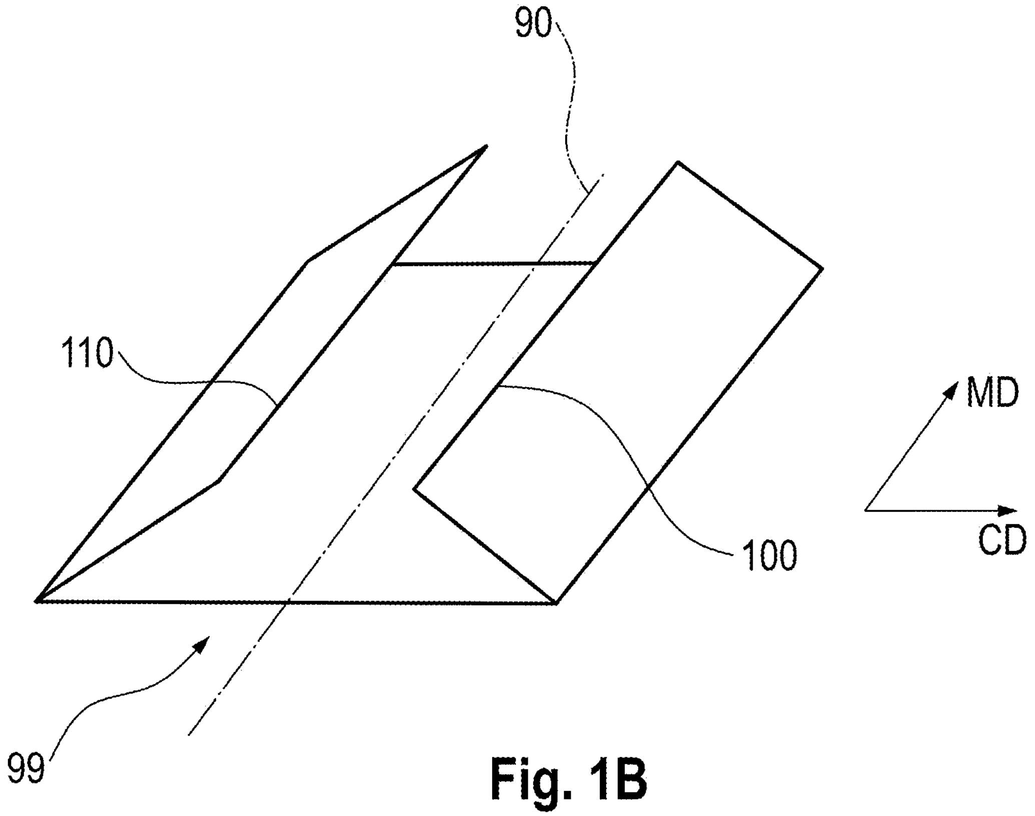
FIG. 1B is a schematic representation showing the package material sheet of FIG. 1A in a partially folded configuration.

Regardless of whether the package material is on rolls or pre-formed to some extent, the packages of the present disclosure begin with paper stock. Referring to FIGS. 1A-1B, edge portions 100 and 110 of a paper stock sheet 99 may be folded towards each other and subsequently sealed to form a seam. For example, side portions 100 and 110 of the sheet 99 may be brought inward towards a longitudinal centerline 90 of the sheet 99 to form a hoop seam 95 (see FIG. 1C). These edge portions may be overlapped with one another and sealed together to form an overlap seam. Alternatively, the edge portions 100 and 110 may be joined together on their respective inner surfaces to form a butt seam. Butt seams tend to not lay as flat as an overlap seam. Therefore, where the seam is located, at least in part, on a bottom panel upon which the package may rest, an overlap seam may be desirable such that the package may sit on a flatter bottom panel.

Figure 1C:
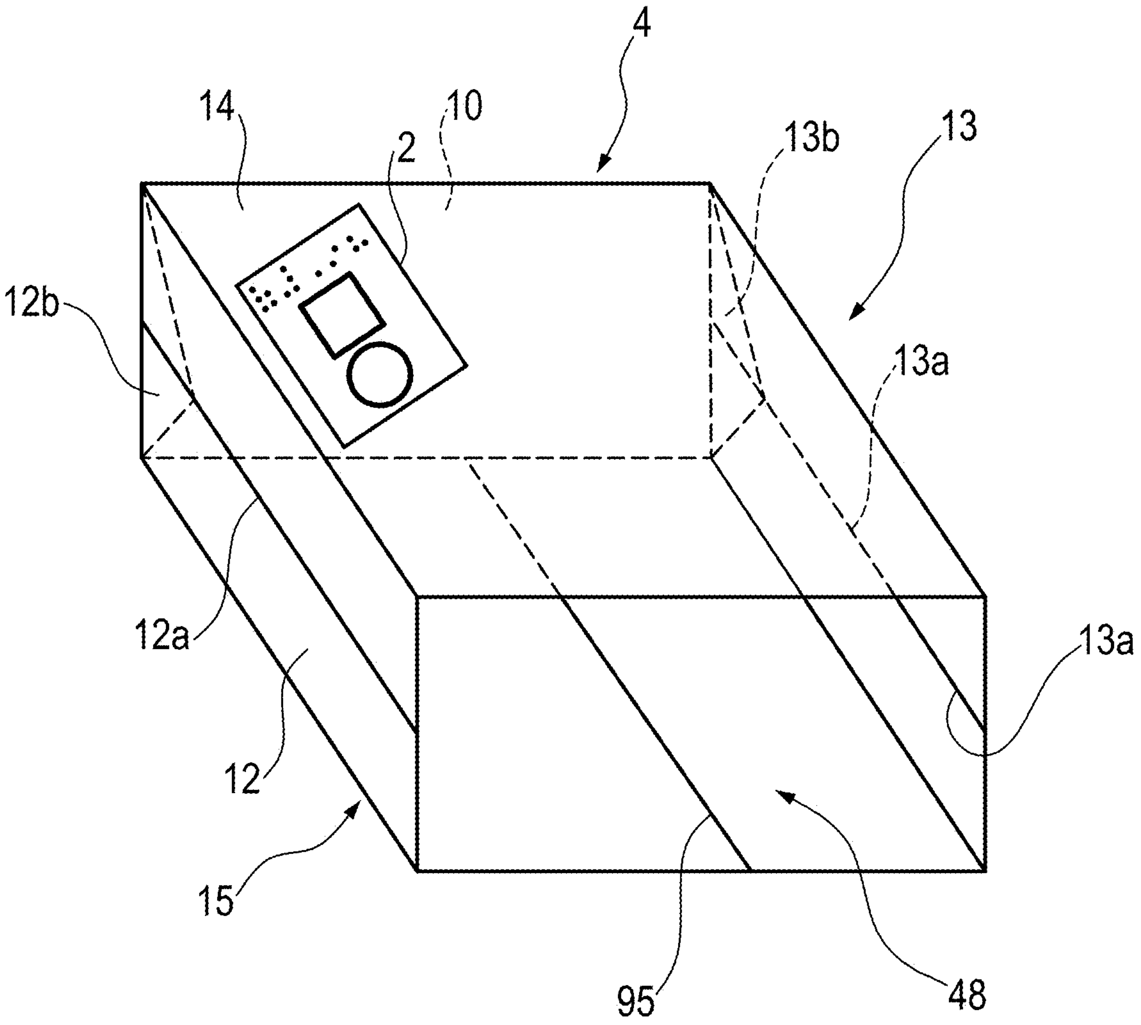
FIG. 1C is a schematic representation of a package with an open end comprising a tactile indicium comprising braille text and rectangular and circular line tactile indicium elements.
Figure 1D:
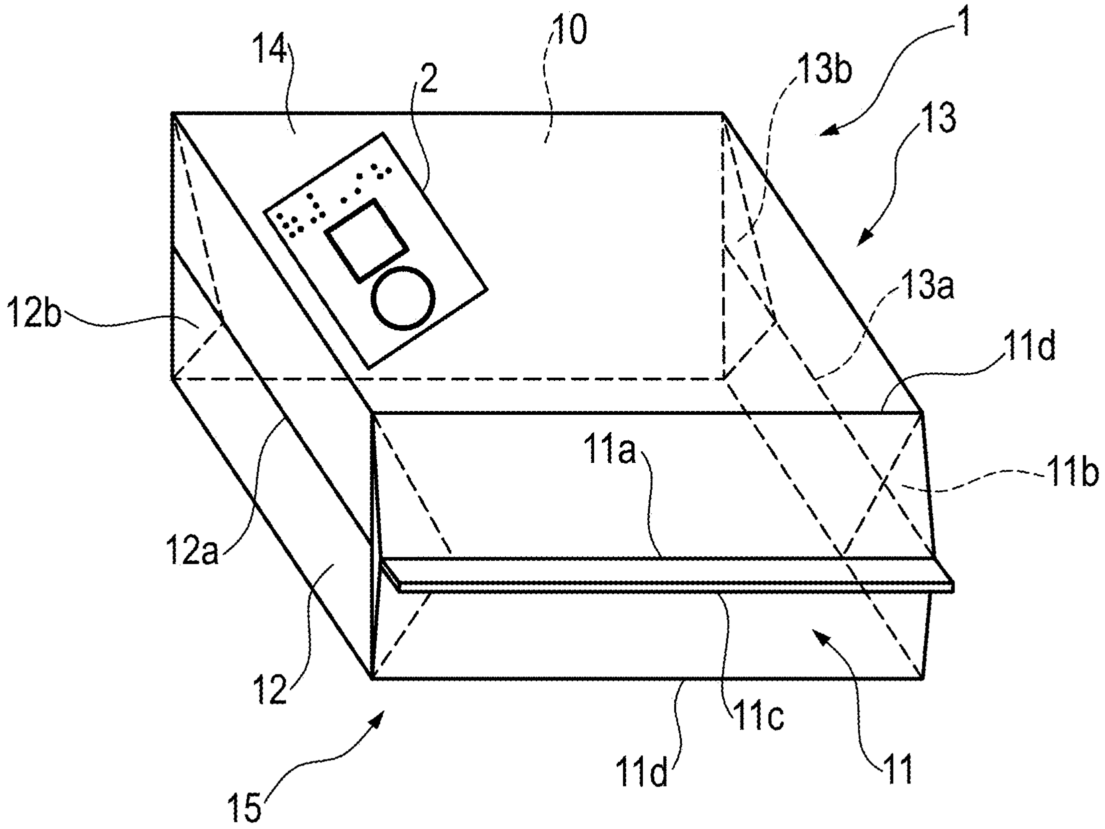
FIG. 1D is a schematic representation of the package of FIG. 1C in a closed state comprising a tactile indicium comprising braille text and rectangular and circular line tactile indicium elements.
Figure 1E:
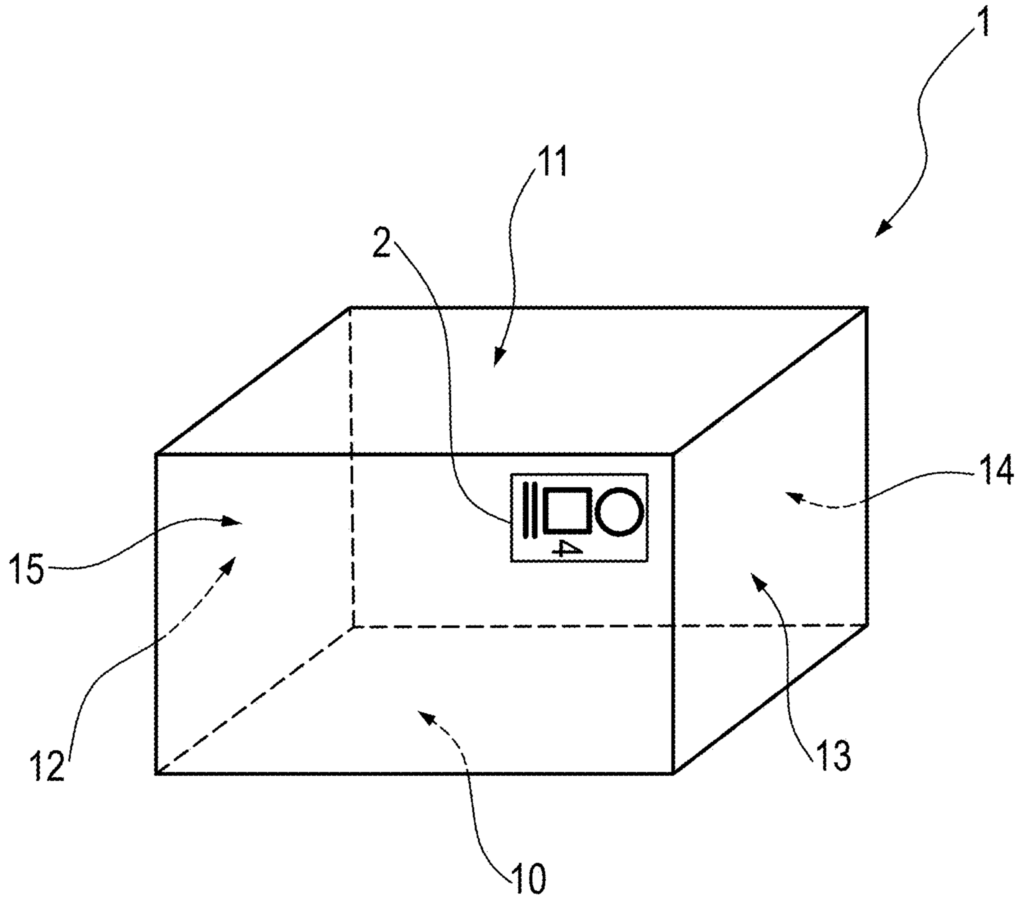
FIG. 1E is a schematic representation of another package of the present disclosure shown in a closed state comprising a tactile indicium comprising two linear, rectangular and circular line tactile indicium elements and a size indicator.

Referring to FIG. 1C-1E, the sheet of packaging material may be suitably folded to form bag side creases 12*b* and 13*b* and two side folds 12*a* and 13*a* on opposite sides, to form the bag structure 4 having a first surface 10, a second and third surface 12, 13, respectively, and a fourth and a fifth surface 14, 15. An open end 48 opposes the first surface 10. Each side crease 12*b*, 13*b* may be located at the respective second or third surface 12, 13. It is worth noting that in FIGS. 1C and 1D, the crease and folds shown are for a package having a block configuration or block bottom configuration. Gussets and fold lines for a pinch bottom bag are discussed in additional detail with regard to FIG. 2B.

The bag 4 may be filled by inserting articles, such as a plurality of absorbent articles, through the open end 48. When the bag 4 is filled with a plurality of articles, e.g., by loading articles from the open end 48, the device used to introduce the articles inside the bag 4 together with the articles may exert some tension on each of the second and third surfaces 12, 13 of the bag 4. For example, the articles may be compressed before being inserted into the bag 4 so that the articles may slightly expand after they are introduced in the bag 4, and thus exert some tension on the second and third surfaces 12, 13 as well as the fourth surface 14 and the fifth surface 15. The tension may be exerted on each of the creases 12*b*, 13*b* at the respective second and third surfaces 12, 13, particularly along the first and second side folds 12*a*, 13*a* by which the package may maintain a substantially parallelepiped shape.

As may be appreciated from FIG. 1D, the open end 48 opposite the first surface 10 may then be closed to form a sixth surface 11. Any suitable style of closing may be utilized. In a form, the sixth surface may comprise closing gussets 11*b*, wherein portions of the outer surface of the package material at the closing gussets 11*b* are brought to form a closing seam 11*a* and a closing seam fin 11*c* extending from the closing seam 11*a*, and sixth surface 11. At least a portion of the closing seam fin 11*c* may be attached to at least a portion of the sixth surface 11. Tacking down the closing seam fin 11*c* to at least a portion of the sixth surface may reduce the risk of unintentional opening of the package, provide for increased stackability, as well provide a cleaner look on-shelf look. Instead of forming closing gussets and a closing fin, the sixth surface may comprise seams which are joined together in a block style configuration or cross style configuration, discussed further herein.

Figure 2A:
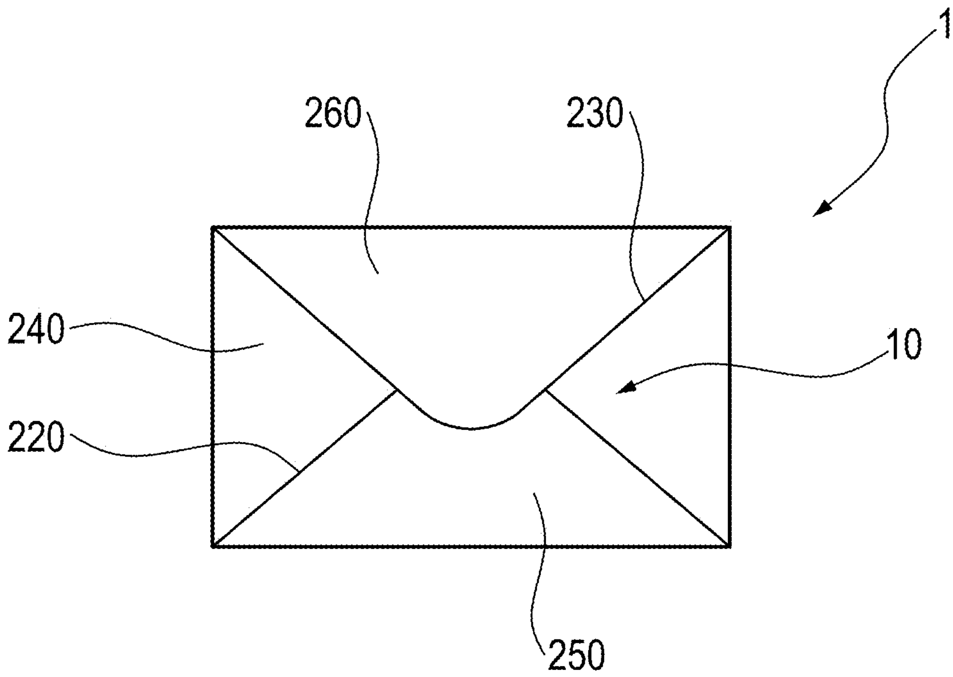
FIG. 2A is a schematic representation showing a panel of a package of the present disclosure, wherein the panel comprises seals in a block bottom configuration.

An example of a block style configuration is shown in FIG. 2A. As shown, the first surface 10 may comprise block style seams 220 and 230. The first surface 10 may comprise a base portion 240. A first flap of package material 250 may be folded onto the base portion 240. First seams 220 may be provided to attach the first flap of package material 250 to the base portion 240. A second flap of package material 260 may be folded onto the base portion 240 and on top of the first flap of package material 250. Second seams 230 may be provided to attach the second flap of package material 260 to the base portion 240 and to the first flap of package material 250. A similar execution may be utilized regarding the sixth surface 11 to form a closure.

Figure 2B:
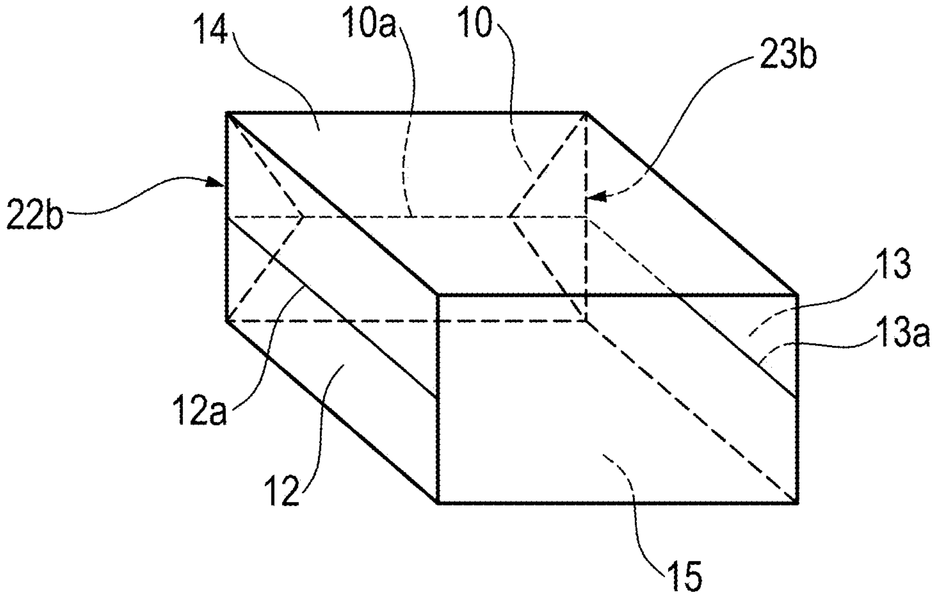
FIG. 2B is a schematic representation showing a panel of a package of the present disclosure, wherein the panel comprises seals in a pinch bottom configuration.

Another example of a panel sealing style which may be utilized with the packages of the present disclosure is the pinch style configuration or the pinch bottom style. An example of a pinch style configuration is shown in FIG. 2B. As shown, one of the key differences between the block bottom and the pinch bottom configuration is the configuration of the creases 12*b* and 13*b*. Instead of creases on the sides 12 and 13, a pinch style configuration comprises gussets 22*b* and 23*b* on the first surface 10. Additionally, in the pinch bottom configuration, the first surface 10 comprises a fold line 10*a* which may be absent in the block style configuration. A similar pinch style configuration may be utilized regarding the sixth surface 11 to form a closure.

Figure 2C:
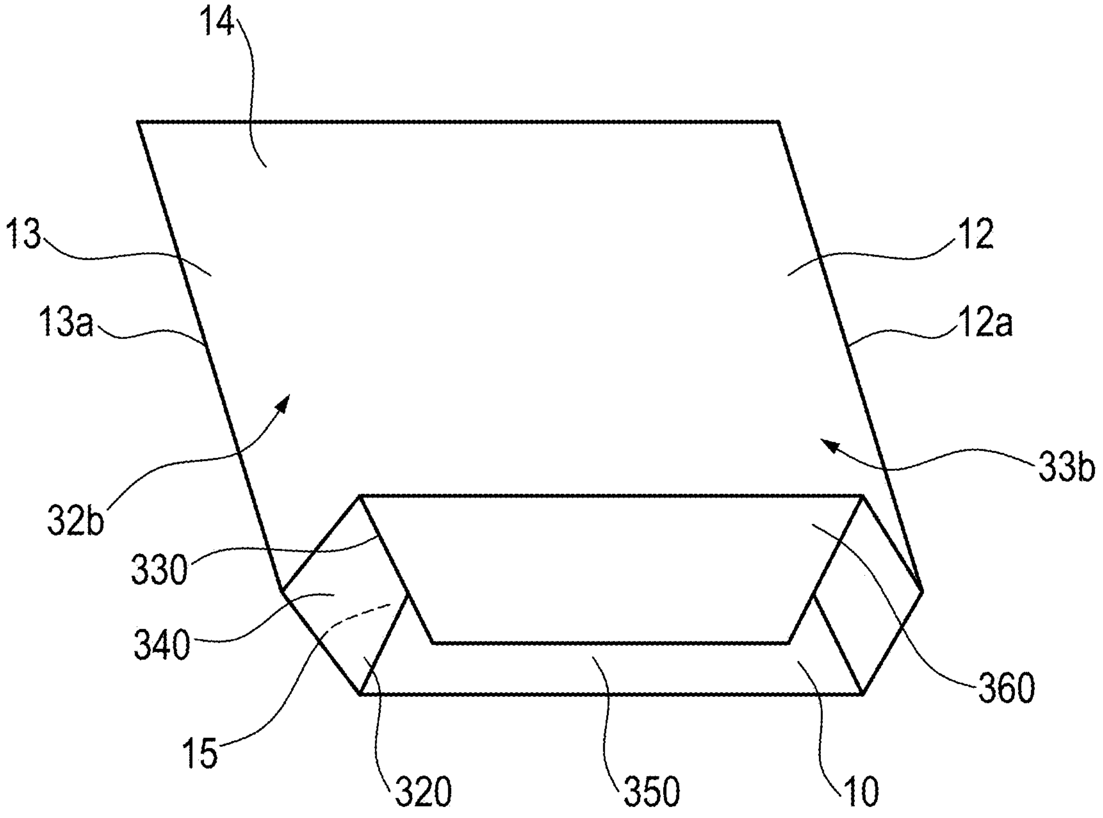
FIG. 2C is a schematic representation showing a panel of a package of the present disclosure, wherein the panel comprises seals in a cross bottom configuration.

Cross style or cross bottom style configurations are also acceptable for sealing portions of the package materials of the present disclosure. An example of a cross style configuration is shown in FIG. 2C. As shown, one of the key differences between the cross style configuration and the block style configuration is that gussets 32*b* and 33*b* and fold lines 12*a* and 13*a* are oriented outward of the interior of the package. In a block-style configuration (FIG. 1C), on the other hand, fold lines 12*a* and 13*a* on the second surface 12 and the third surface 13, respectively, are oriented inward prior to filling the package. Due to the orientation of the gussets 32*b* and 33*b* in the cross style configuration, filling the package with absorbent articles may require less energy to expand the package for filling. As an example, creases oriented inward, e.g., block style configuration, would require displacement outward of the creases prior to filling the package. Additionally, the equipment utilized in guiding the product into the package may have a reduced likelihood of interfering with the gussets, given their orientation outward. This may reduce the likelihood of packaging mishaps or manufacturing process stoppages due to quality issues.

Referring again to FIG. 2C, similar to the block style configuration, the first surface 10 of the cross style configuration comprises seams 320 and 330. The first surface comprises a base portion 340. A first flap of package material 350 may be folded onto the base portion 340. First seams 320 may be provided to attach the first flap of package material 350 to the base portion 340. A second flap of package material 360 may be folded onto the base portion 340 and on top of the first flap of package material 350. Second seams 330 may be provided to attach the second flap of package material 360 to the base portion 340 and/or to the first flap of package material 350. A similar execution may be utilized to form the closure on the sixth surface (formed once the package is sealed after the placement of absorbent articles therein).

For less bulky items, where standability of the package is desired, the block bottom or cross bottom may be desirable, as these configurations form a flat base. However, for bulky items, the pinch style configuration bags may be beneficial as the bulky absorbent articles therein may form a steady base for the package to stand. The inventors have surprisingly found that diapers may be suited for pinch bottom bags due their bulky nature. In contrast, feminine hygiene articles, particularly menstrual pads, may be suited for block bottom configured packages.

Additionally, it is worth noting that block style and cross style configured packages tend to be themselves bulkier than their pinch style counterparts. For the purposes of packaging absorbent articles, unfilled packages may arrive pre-formed in stacks to an absorbent article manufacturer. Typically, stacks of pre-formed block style and cross style configuration packages will take up more space—due to their bulkiness—as compared to pre-formed pinch style packages. The bulkiness of the block and cross style configurations may make the stacks more difficult to manipulate during the filling process, particularly where a large number of filled packages are created per minute. In such instances, the bulkiness of these configurations may mean an increased frequency of replenishment of the stacks.

Referring back to FIGS. 1C-1D, the first surface 10 may form at least a portion of the top panel of the package 1. In another embodiment, the first surface 10 may form at least a portion of the bottom panel of the package 1. It is worth noting that if the first surface 10 comprises seams, it may be desirable that the first surface 10 forms at least a portion of the bottom panel. In this way the seams may be hidden from view on the store shelf. The second and third surfaces 12 and 13, as they may comprise gussets 12*b* and 13*b*, respectively, may form at least a portion of a first side panel and opposite second side panel, respectively, or vice versa. The fourth and fifth surfaces 14, 15 may form at least a portion of a front panel and an opposite back panel, respectively, or vice versa. At least one of the fourth and/or fifth surface 14, 15, may comprise branding, product information and/or background color as described herein, as the front panel is generally the consumer-facing panel. However, product information and/or background color may not be limited to the consumer-facing panel. Any combination of the panels of the packages of the present disclosure may comprise branding, product information, and/or background color. The sixth surface 11 may form at least a portion of the top panel or at least a portion of the bottom panel of the package 1. Where the sixth surface 11 comprises closing gussets 11*b*, closing seam 11*a*, and a closing seam fin 11*c* extending from the closing seam 11*a*, it may be desirable that the sixth surface 11 forms at least a portion of the top panel. In this way the closing gussets 11*b* and closing seam fin 11*c* do not introduce bulk and instability to the base of the package. Where the sixth surface 11 forms at least a portion of the top panel, a top edge region 11*d* is formed at the transition from the top panel to the front, back, and first and second side panels. The top edge region 11*d* may be formed by portions of the top, front, back, first side, and second side panels that are adjacent to a fold in the package material designating a transition from the top panel to another panel.

The closing seam fin 11*c* may comprise a carrying handle 1200, as shown in FIGS. 6, 12A-16, and 18A. The carrying handle 1200 may be formed by a portion of the closing seam fin 11*c* that is devoid of packaging material. In a form, as least a portion of the packaging material forming the closing seam fin 11*c* may be excised to define the carrying handle 1200. The carrying handle 1200 may be configured to allow a user to engage the carrying handle 1200 without needing to grasp the handle with the user's hands. For example, the carrying handle 1200 may be sized to allow a user to slip their entire hand through the carrying handle 1200, and hook the carrying handle 1200 around the user's wrist, thus keeping the user's hand free. As such, the area defining the carrying handle 1200 may measure at least 100 $cm^2$, at least 150 $cm^2$, at least 200 $cm^2$, or at least 250 $cm^2$.

Figure 7:
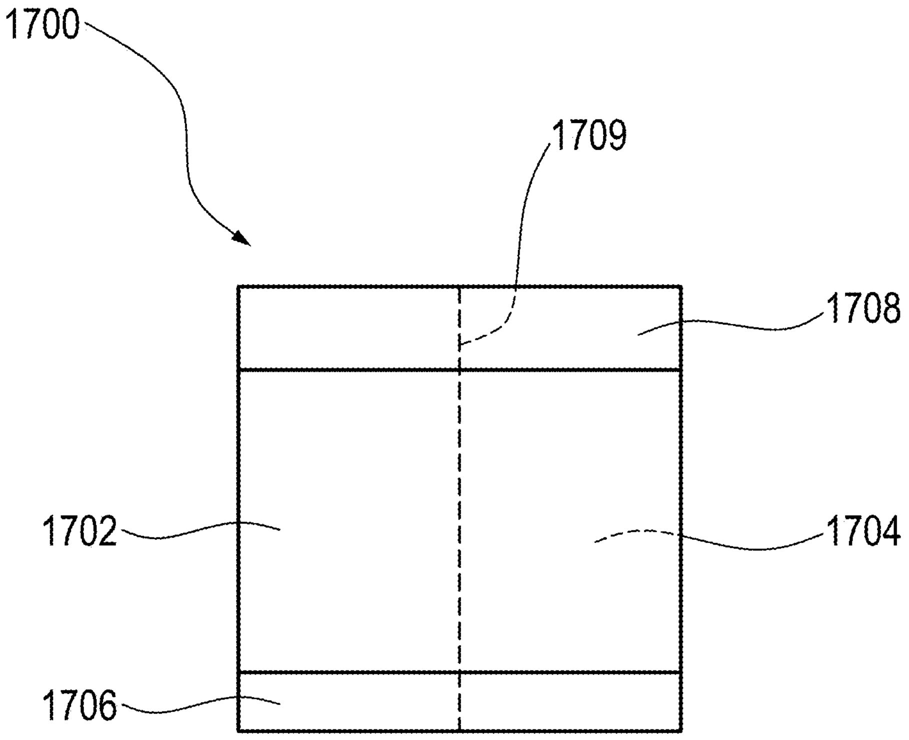
FIG. 7 is a schematic plan view of a package of the present disclosure constructed with a flow wrap process.

Other package shapes are contemplated. Examples of such packages include flow wrap or horizontal form fill-and-seal wrap. Such packages may comprise a generally cuboid shape also configured as described above. However, in some instances, such as shown in FIG. 7, a flow wrap package 1700 may comprise a first surface 1702 and an opposing second surface 1704. Rounded edges may be provided as a transition between the first surface 1702 and the second surface 1704. In another form, one or more fold lines may be provided between the first surface 1702 and the second surface 1704. The flow wrap package 1700 may further comprise end seals 1706 and 1708, and a hoop seam 1709 which may be disposed on the second surface 1704. In such packages, the first surface 1702 may comprise the consumer-facing panel. Flow wrap packages may be useful, particularly where a low number of absorbent articles are included within a package.

Figure 8A:
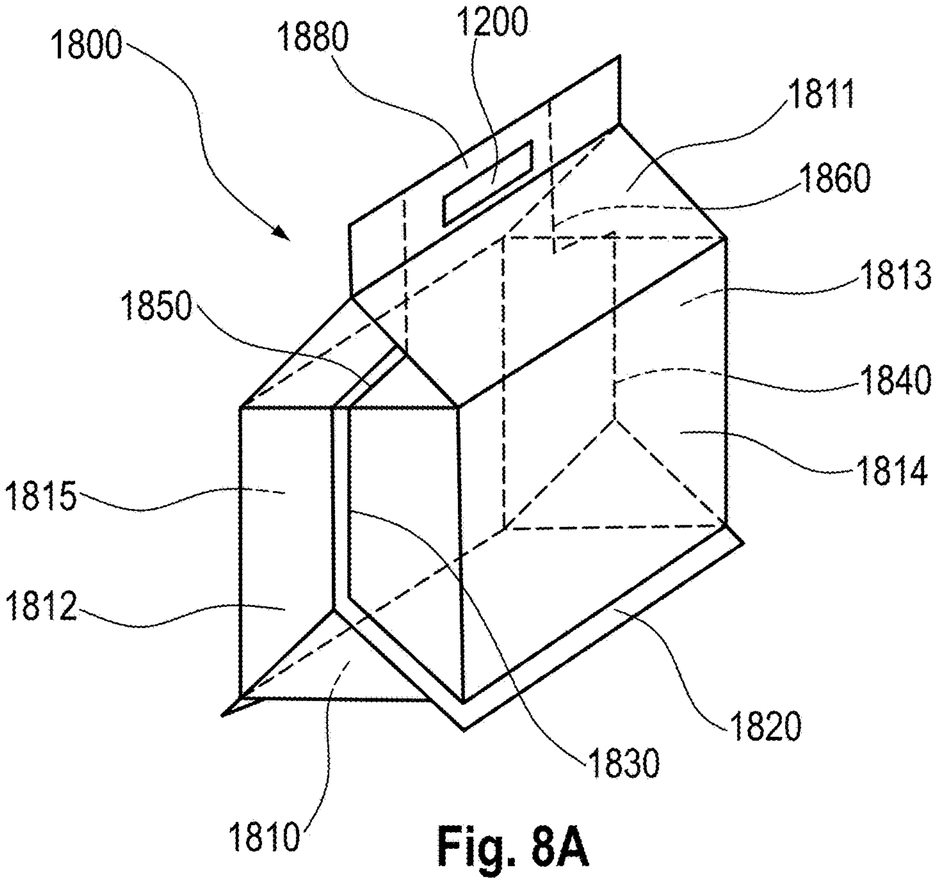
FIG. 8A is a schematic representation of a package configuration in accordance with the present disclosure constructed in accordance with the present disclosure.
Figure 8B:
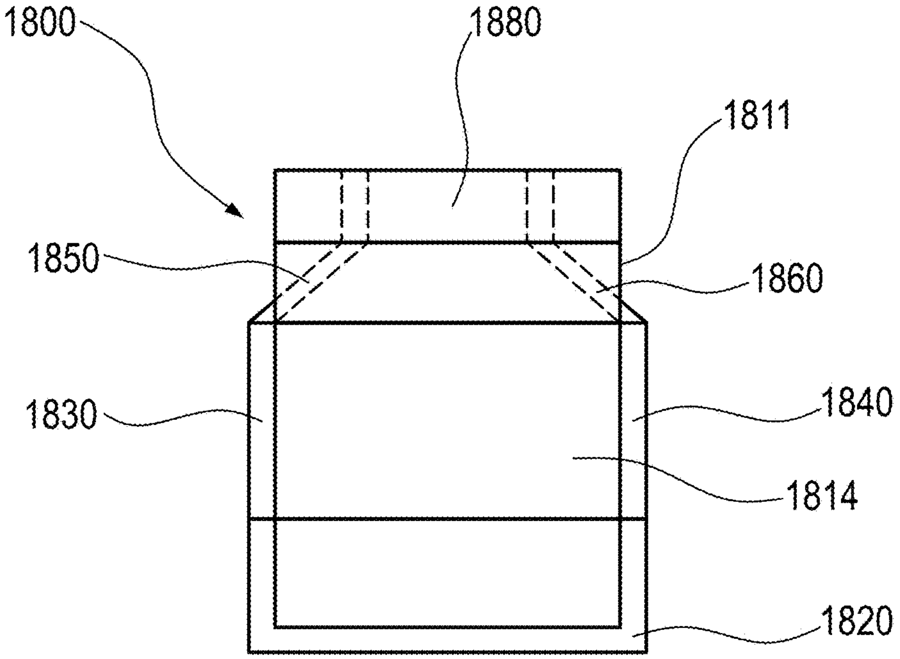
FIG. 8B is a schematic representation of a front view of the package configuration of FIG. 8A.

Another package form in accordance with the present disclosure may comprise seams/seals which are move overt than those packages comprising a block bottom, pinch bottom, and/or cross bottom. Referring to FIGS. 8A and 8B, a package 1800 is shown. The package 1800 may be configured in generally a cuboid shape. The package 1800 may comprise a first panel 1811, opposing second and third panels 1812 and 1813, opposing fourth and fifth panels 1814 and 1815, and a sixth panel 1810 opposing the first panel 1811. As shown, between the fourth panel 1814 and the sixth panel 1810, a first seal 1820 extends outward. The first seal 1820 may form a sort of foot for the package 1800. A second seal (not shown) may extend outward between the fifth panel 1815 and the sixth panel 1810 in a similar fashion to the first seal 1820.

The first seal 1820 can extend such that a portion of the first seal 1820 is on the second panel 1812 and another portion of the first seal 1820 is disposed on the third panel 1813. Similarly, a portion of the second seal may be disposed on the second panel 1812 and another portion may be disposed on the third panel 1813. The first seal 1820 and the second seal may be provided where the sixth panel 1810 is formed from a discrete piece of material which is subsequently joined to the fourth panel 1814 and fifth panel 1815. Of course, forms where the sixth panel 1810 is unitary with the fourth panel 1814 and fifth panel 1815 are also contemplated.

A third seal 1830 and a fourth seal 1840 may extend outward from the second panel 1812 and the third panel 1813, respectively. It is worth noting that the first seal 1820, second seal, third seal 1830, and fourth seal 1840 collectively may comprise the hoop seal discussed herein. Thus, one, all, or any combination, of these seals may exhibit the tensile strength for the hoop seal as described herein.

As shown, the package 1800 may further comprise a fifth seam 1850 and a sixth seam 1860 which are disposed on the sixth panel 1811. The fifth seam 1850 and sixth seam 1860 can extend into a seal fin 1880. It is worth noting that the package 1800 and the seams associated therewith, may be assembled as described herein regarding adhesives, barrier films, and/or combinations of barrier films and adhesives. However, the construction of the package 1800 is particularly well suited for the creation of seams via barrier film coating on an inner surface of the package material. In such configurations, the film may form a barrier that reduces the likelihood or at least the amount of moisture vapor through the package material to the absorbent articles therein.

Figure 9A:
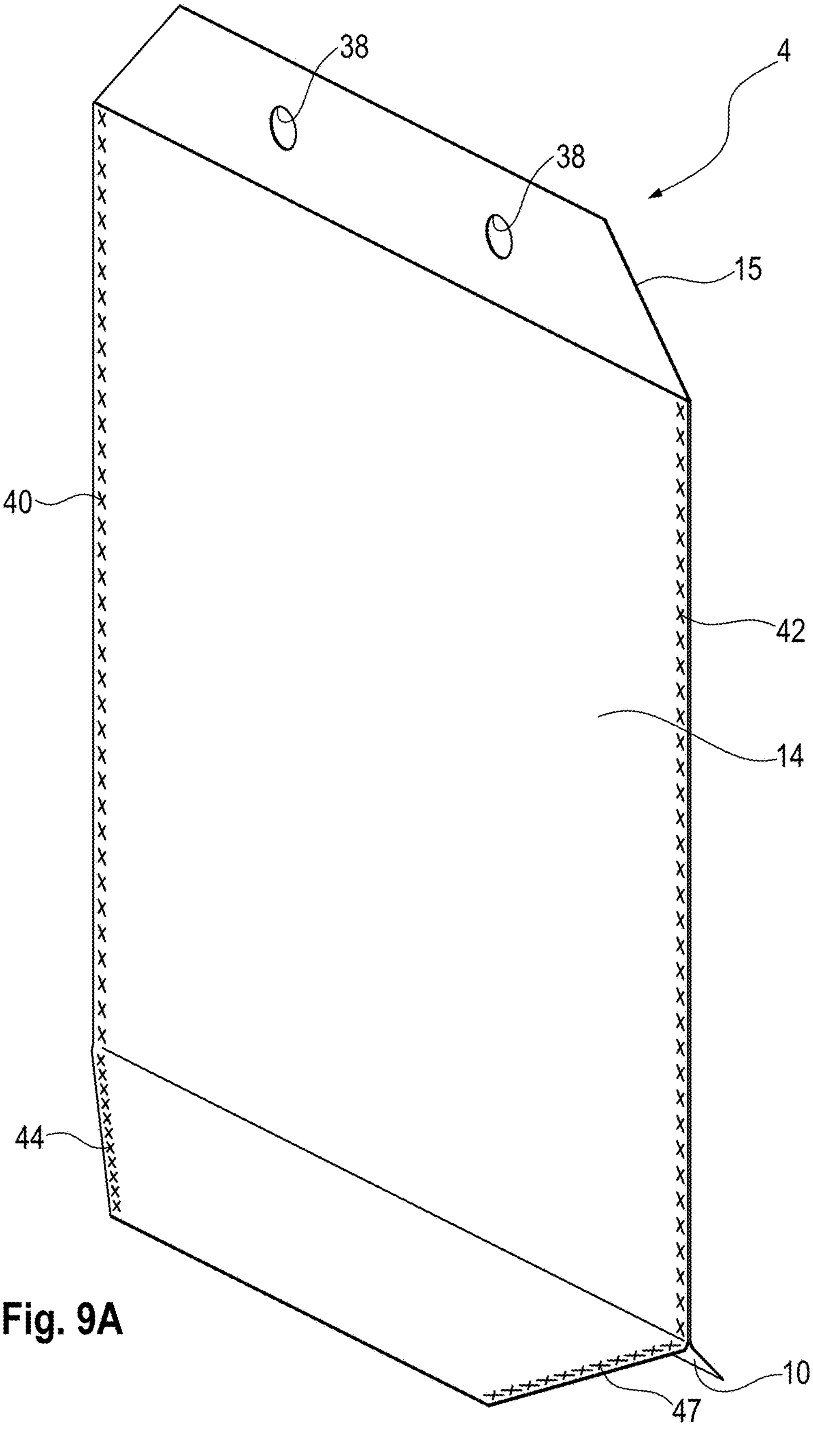
FIG. 9A is a perspective view of a bag of the present disclosure in a partially flattened configuration and without one or more absorbent articles within the bag.
Figure 9B:
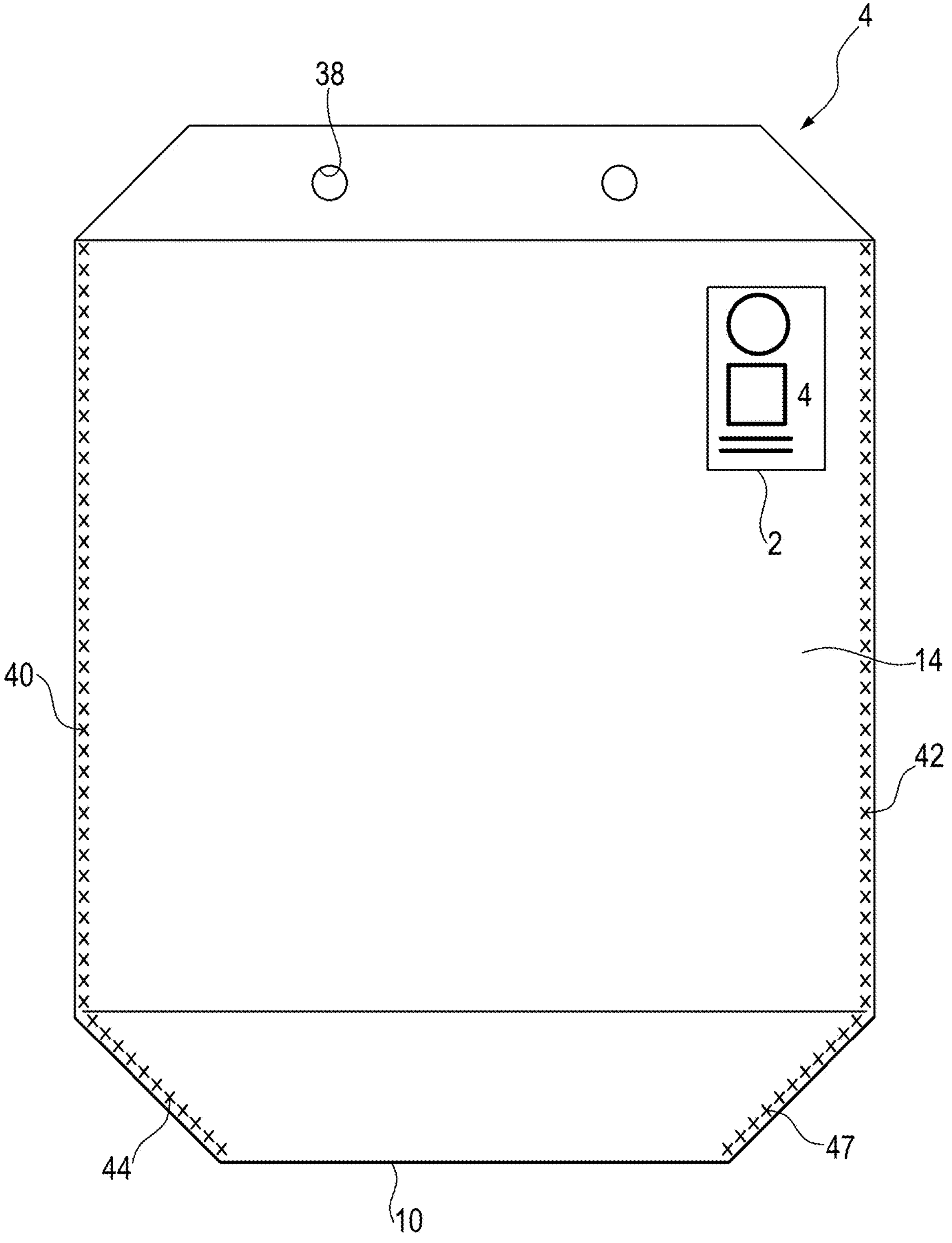
FIG. 9B is a front view of the bag of FIG. 9A.
Figure 9C:
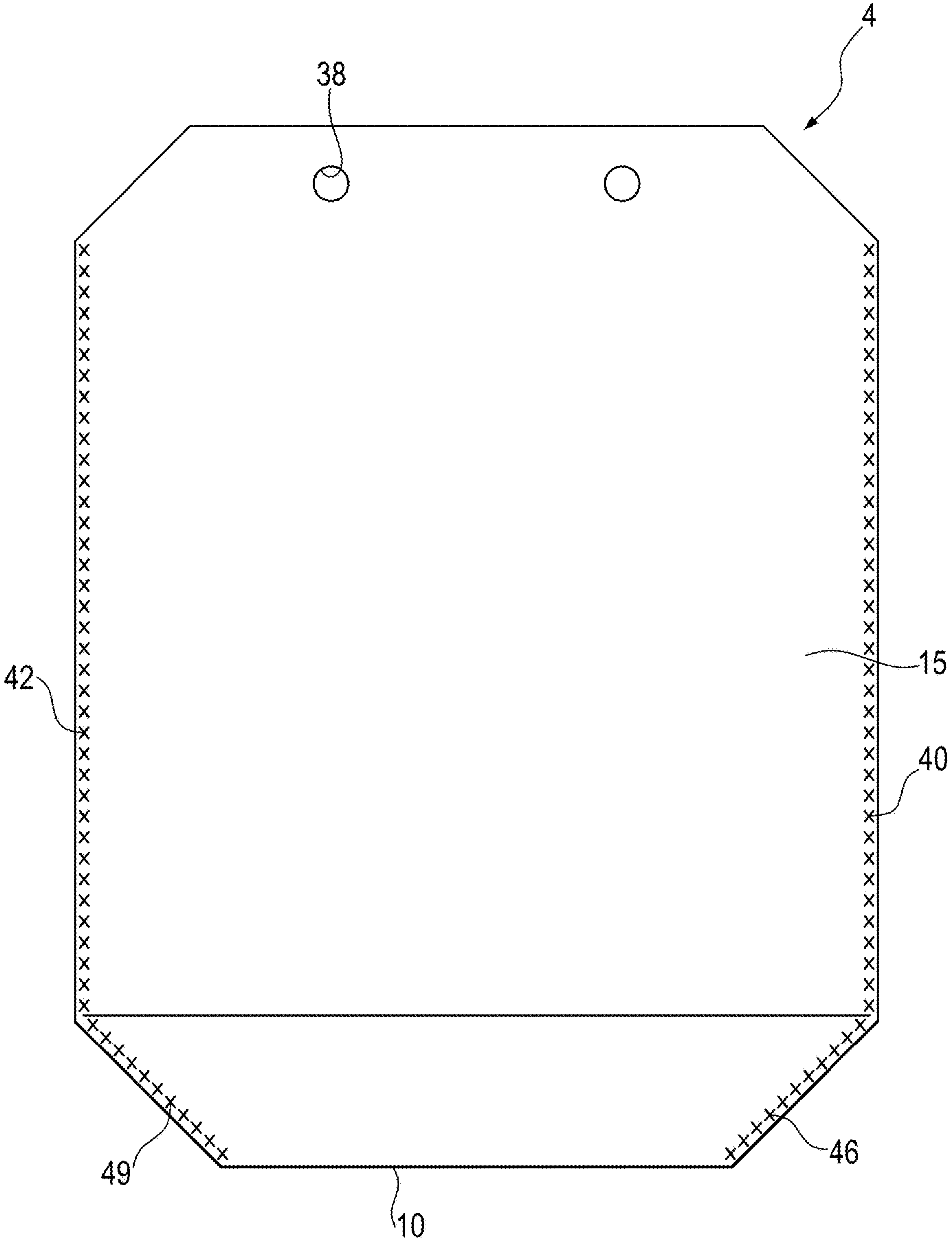
FIG. 9C is a back view of the bag of FIG. 9A.
Figure 9D:
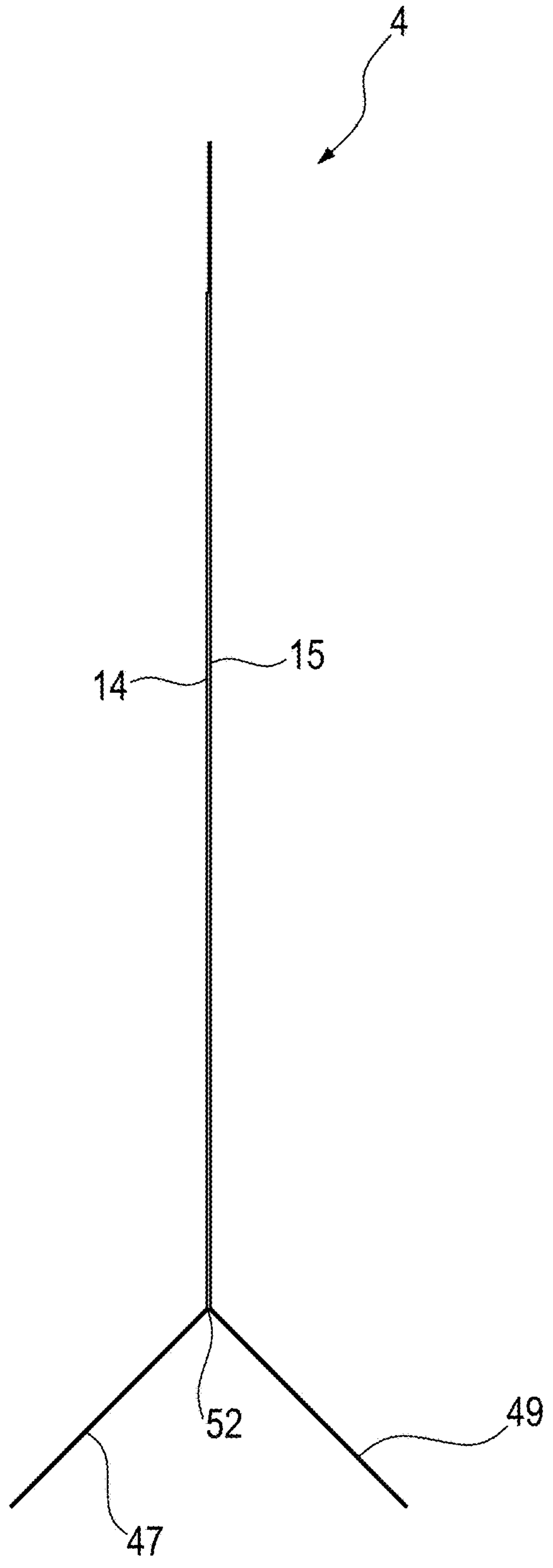
FIG. 9D is right side view of the bag of FIG. 9A, with the left side view being identical.
Figure 9E:
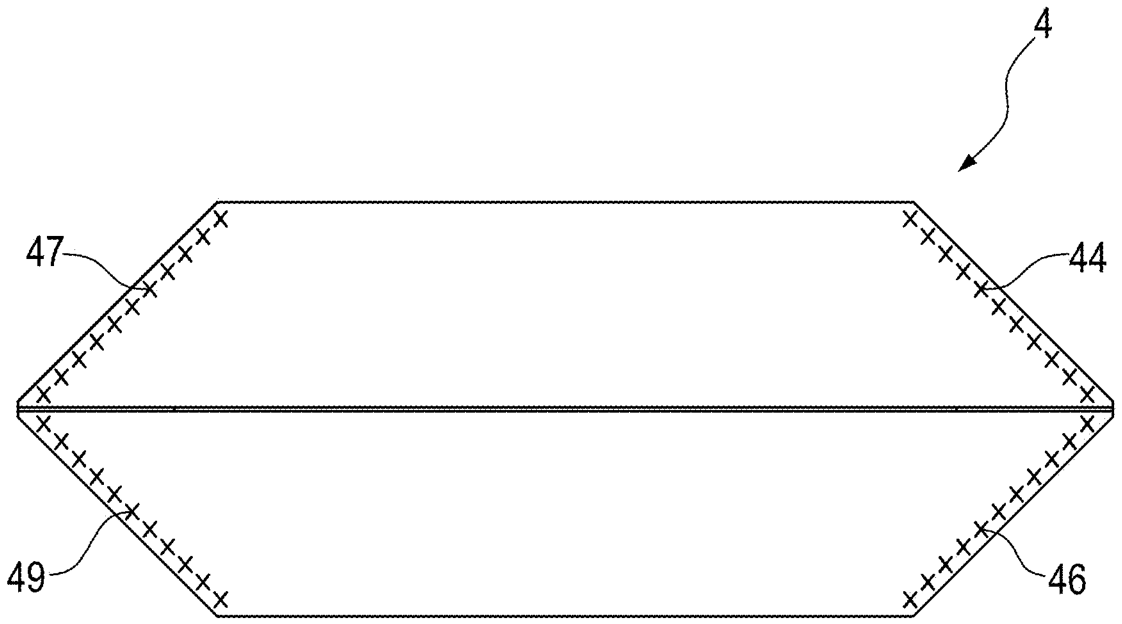
FIG. 9E is a top view of the bag of FIG. 9A.
Figure 9F:
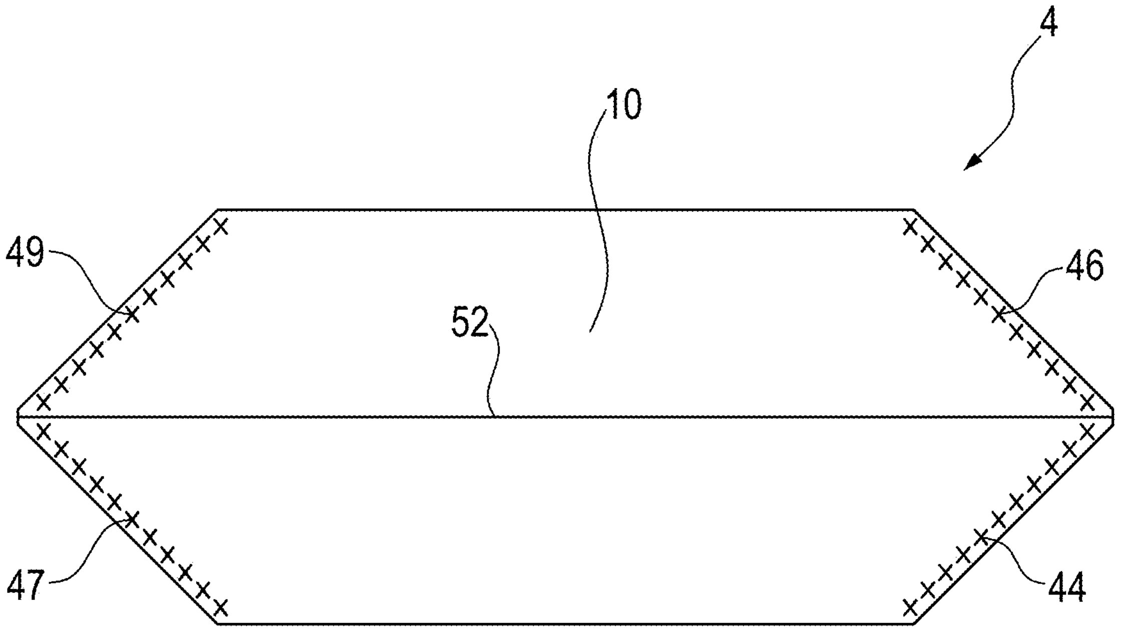
FIG. 9F is a bottom view of the bag of FIG. 9A.
Figure 9G:
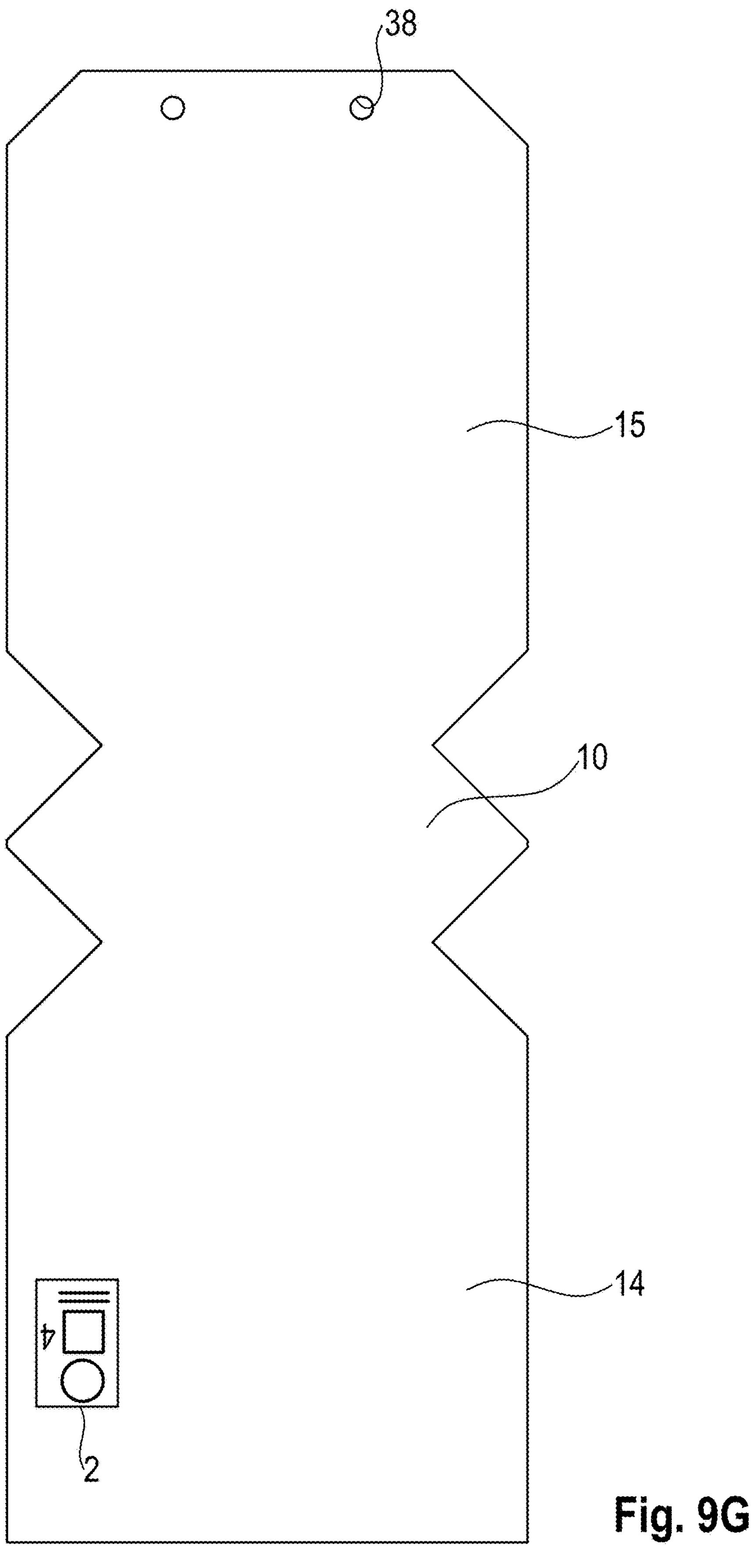
FIG. 9G is a view of a shape of the packaging material used to produce the bag of FIG. 9A.

An example flattened bag 4—prior to adding one or more absorbent articles—of the present disclosure is disclosed. The bag 4 may have the configuration illustrated in FIGS. 9A-9F. FIG. 9A is a perspective view of a bag 4 of the present disclosure in a partially flattened configuration and without one or more absorbent articles within the package. FIG. 9B is a front view of the bag of FIG. 9A. FIG. 9C is a back view of the bag 4 of FIG. 9A. FIG. 9D is right side view of the bag of FIG. 9A, with the left side view being identical. FIG. 9E is a top view of the bag of FIG. 9A. FIG. 9F is a bottom view of the bag of FIG. 9A. FIG. 9G is a view of a shape of the packaging material used to produce the bag 4 of FIG. 9A, the package 1 respectively. Referring to FIGS. 9A-9F, the bag may comprise a fourth surface 14, a fifth surface 15, a left side panel 12 and a right side panel 13 (that are only formed when absorbent articles are within the bag 4, package 1 respectively), a bottom panel 10, and a first and a second part of the top panel 11 (that are formed when absorbent articles are within the package 1 and the package 1 is sealed). Portions of the fourth surface 14 and the fifth surface 15 will eventually form the left 12 and right side panels 13 and the top panel 11 when the package is filled with absorbent articles.

The bag 4 may be designed to have two wicket holes 38. At times, there may be one wicket hole or more than two wicket holes. In an instance, a single wicket hole may form an elongated hole. The portion of the bag 4 having the wicket holes 38 may be cutaway when the package 1 is sealed. As such, consumers will not see the wicket holes 38. In other instances, the bag 4 may be wicketless (i.e., not have one or more wicket holes). Front panel 14, the bottom panel 10, the back panel 15, and the top panel 11 may be formed of a continuous material.

Figure 9H:
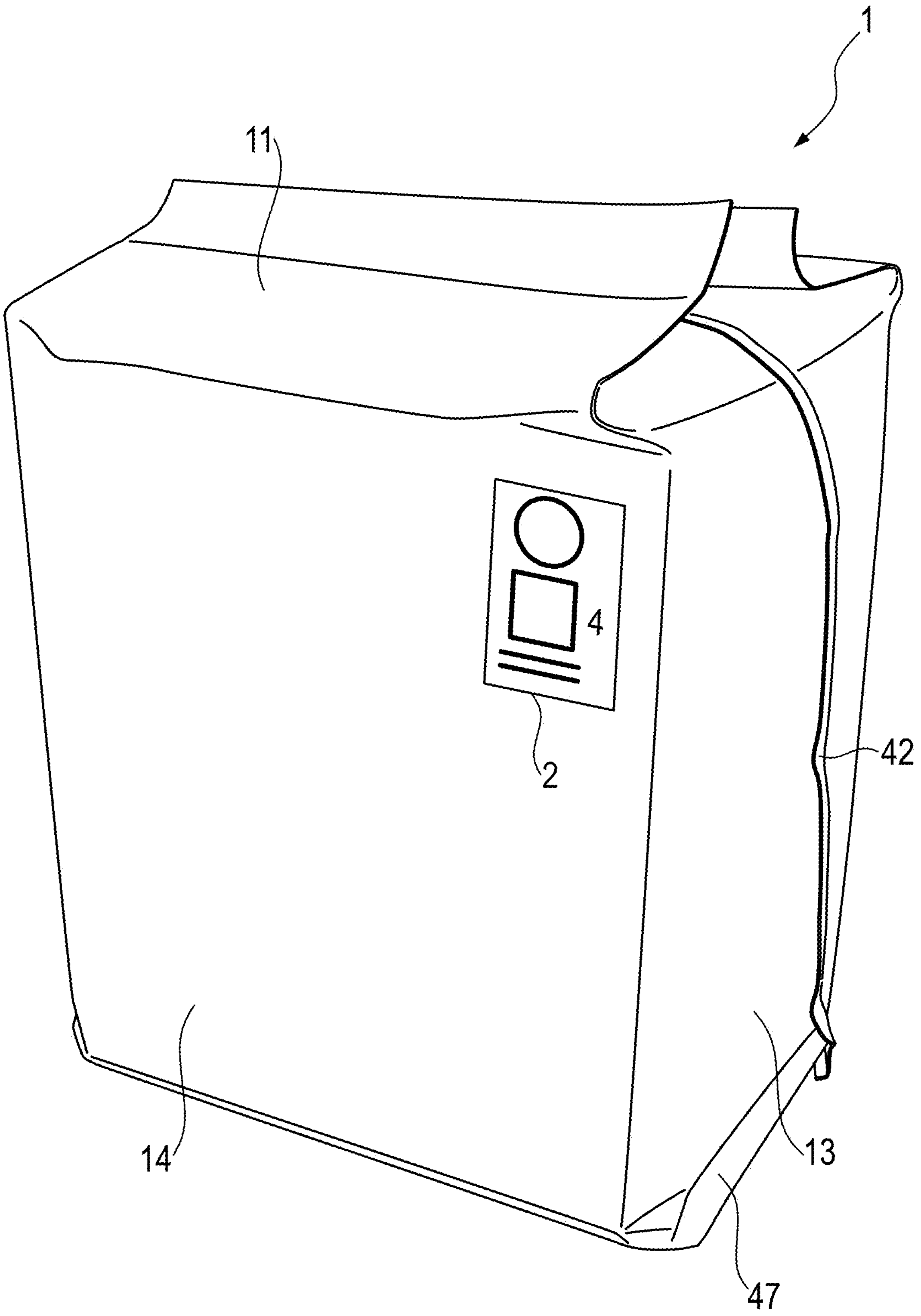
FIG. 9H is a front right side perspective view of an example package with a plurality of absorbent articles positioned therein of the present disclosure.

A vertical left side seam 40 may be formed at the location shown in FIGS. 9A-9C. The vertical left side seam 40, although illustrated in FIGS. 9A-9C as on the fourth surface 14, which forms the front panel 14 of the package 1, and the fifth surface 15, which forms the back panel 15 of the package 1, will be on the left side panel 12 when one or more absorbent articles are added to the bag 4. A vertical right side seam 42 may be formed at the location shown in FIGS. 9A-9C. The vertical right side seam 42, although illustrated in FIGS. 9A-9C as on the fourth surface 14, which forms the front panel 14 of the package 1, and the fifth surface 15, which forms the back panel 15 of the package 1, will be on the right side panel 13 when one or more absorbent articles are added to the bag 4. A first left side angled seam 44 may be formed between portions of the fourth surface 14, the front panel 14 respectively, and portions of the first surface 10, bottom panel 10 respectively. A second left side angled seam 46 may be formed between portions of the fifth surface 15, the back panel 15 respectively, and portions of the first surface 10, bottom panel 10 respectively. A first right side angled seam 47 may be formed between portions of the fourth surface 14, the front panel 14 respectively, and portions of the first surface 10, bottom panel 10 respectively. A second right side angled seam 49 may be formed between portions of the fifth surface 15, the back panel 15 respectively, and portions of the first surface 10, bottom panel 10 respectively. When the bag 4 is filled with one or more absorbent articles, the angled seams 44 and 46 may be formed on the left side panel 12 and the angled seams 48 and 50 may be formed on the right side Panel 13. Any of the seals or seams may form overlap seams and/or butt seams as described herein. The bag 4, package 1 respectively, may also comprise a fold line 52 in first surface 10, bottom panel 10 respectively. FIG. 9H shows an example package 1 of the present disclosure formed from a bag 4 shown in FIGS. 9A-9F.

Package shapes are also contemplated where the package comprises less than six panels. Packages having a circular or semi-circular shape when viewed from a bottom panel are contemplated. Additionally, packages having a triangular shape when viewed from the bottom panel are contemplated. Regardless of the number of panels comprised by the packages of the present disclosure, the package comprises a consumer-facing panel.

Absorbent Article Configuration

The packages of the present disclosure comprise one or more compressed absorbent articles. The absorbent articles may be placed into the package in an unfolded or folded configuration. The articles may be folded laterally and/or longitudinally. The articles may comprise one fold line, and may be disposed within the package in a bi-fold configuration. The articles may comprise two fold lines, and may be disposed within the package in a tri-fold configuration.

Figure 3A:
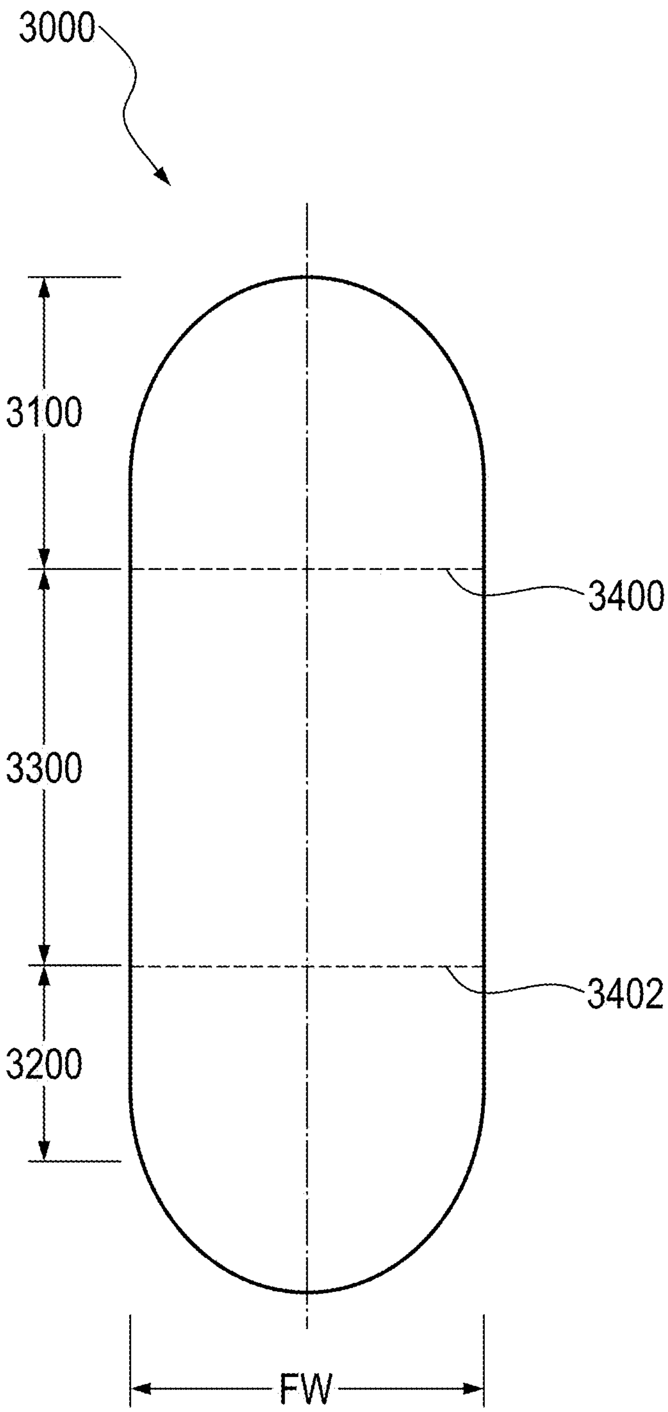
FIG. 3A is a plan view of an example of an absorbent article in the form of a feminine hygiene pad in an unfolded configuration.
Figure 3B:
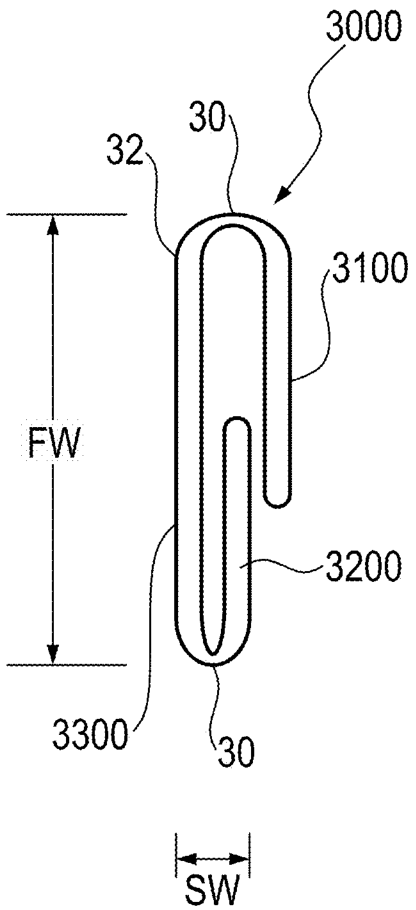
FIG. 3B is an edge side view of the feminine hygiene pad of FIG. 3A, shown folded about lateral fold lines in a tri-fold configuration.

FIG. 3A depicts an example of a feminine hygiene pad in an unfolded configuration. FIG. 3B depicts a side view of the feminine hygiene pad of FIG. 3A in a tri-fold configuration. The feminine hygiene pad depicted in FIGS. 3A and 3B comprises a first fold line 3400 disposed between a first end region of the pad 3100 and a central region of the pad 3300, and a second fold line 3402 disposed between a second end region of the pad 3200 and the central region 3300. Prior to placement within the package, the second end region 3200 may be folded over and longitudinally inward about the second fold line 3402 to overlap at least a portion of the central region 3300, as may be appreciated from a comparison of FIGS. 3A and 3B. The first end region 3100 may then be folded over and longitudinally inward about the first fold line 3400 to overlap at least a portion of the central region 3300 and a portion of the second end region 3200. In some examples a tri-fold configuration may have the article folded approximately in thirds, about the two longitudinally-spaced lateral fold lines.

Figure 4A:
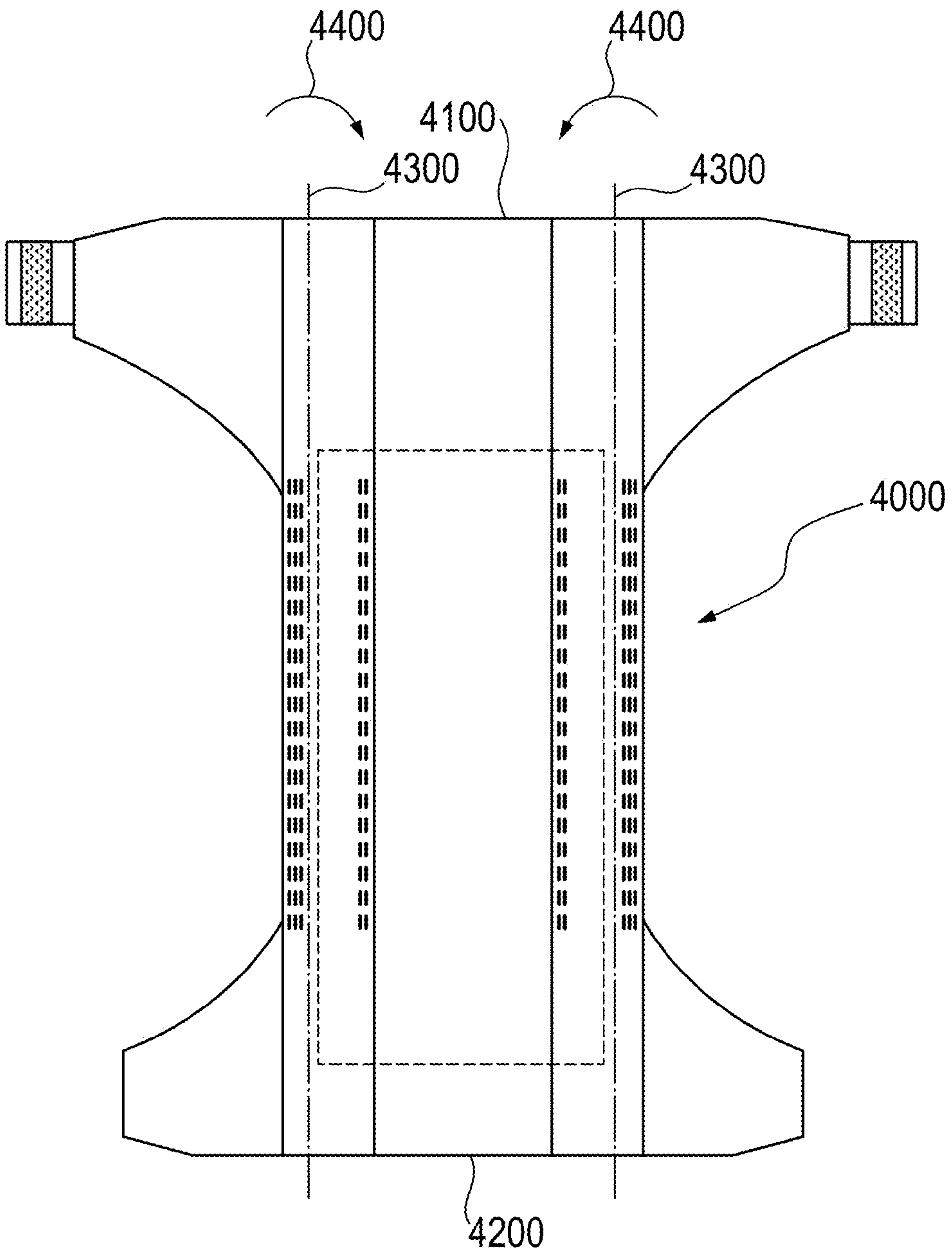
FIG. 4A is a plan view of an example of an absorbent article in the form of a disposable diaper, wearer-facing surfaces facing the viewer.
Figure 4B:
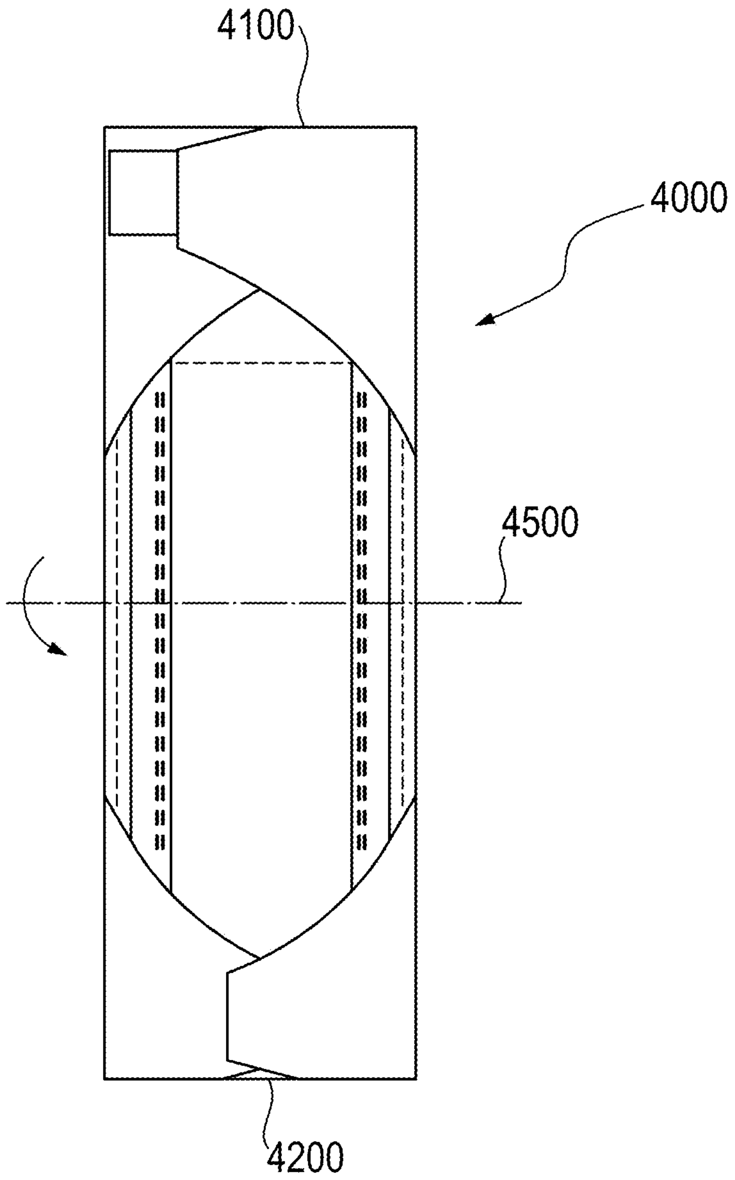
FIG. 4B is a plan view of the diaper of FIG. 4A, shown with side portions folded over and laterally inward about longitudinal side edge fold lines.
Figure 4C:
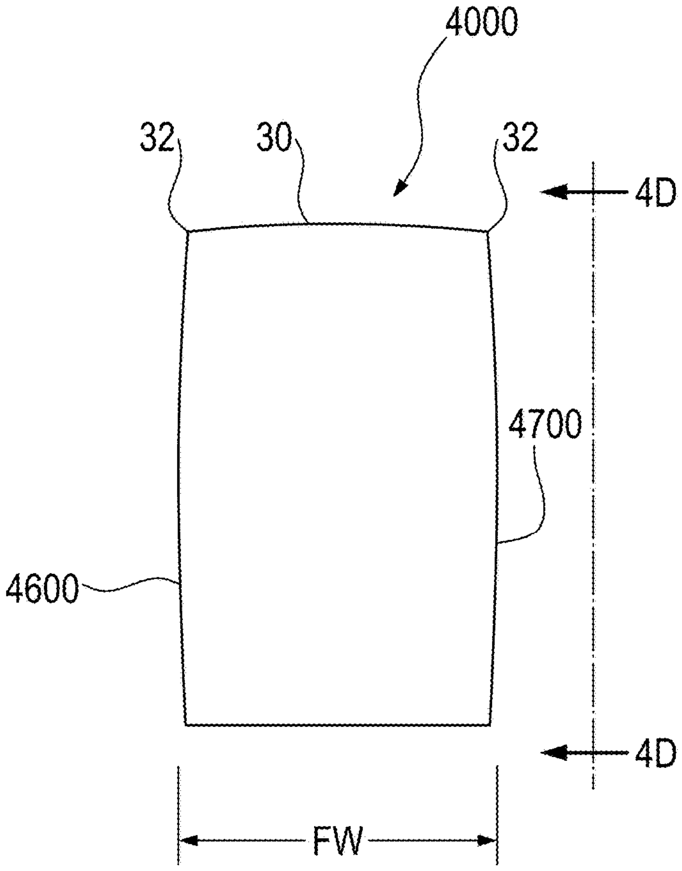
FIG. 4C is a plan view of the diaper of FIG. 4B, shown folded about a lateral fold line, wearer-facing surfaces in and outward-facing surfaces out.
Figure 4D:
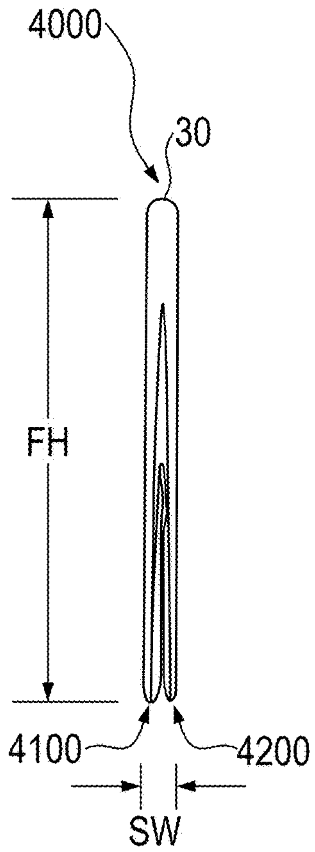
FIG. 4D is a side view of the folded diaper shown in FIG. 4C.

FIGS. 4A-4D depict an absorbent article in the form of a diaper 4000 with front and rear waist edges 4100, 4200, in successively open/unfolded and folded configurations. For packaging in bulk, each of a plurality of diapers such as that shown in FIG. 4A may, in a possible first step, have its longitudinal side portions be folded over and laterally inward about longitudinal side edge fold lines 4300, as may be appreciated from a comparison of FIGS. 4A and 4B. Next, the diaper may, in a second step, be folded longitudinally, about lateral fold line 4400 that passes through the crotch region of the diaper, as may be appreciated from a comparison of FIGS. 4B and 4C. For a bi-fold configuration such as depicted in FIGS. 4C and 4D, the article may be folded longitudinally once, and may in some examples be folded approximately in half about the lateral fold line 4400.

Regardless of whether the article is in a bi-fold or tri-fold configuration, the folded article, such as folded feminine hygiene pad 3000 and/or folded diaper 4000, may have a single fold nose 30 defining at least one end edge of the folded article, fold nose corners 32, and left and right longitudinal peripheral edges 4500, 4600. It will be appreciated that in a tri-fold example, a single fold nose may define each of both end edges of the folded article. In some examples, such as depicted in FIGS. 4C and 4D, fold nose 30 may be proximate the crotch region of the article (the middle region of the article adapted to be located between the wearer's legs during wear). The folded article will have a folded width FW measured as the distance between side edges, a folded height FH measured as the distance between fold nose 30 and the end edges (in the case of a bi-fold configuration) or between the two fold noses 30 (in the case of a tri-fold configuration), and a side width (SW). The folded width (FW) forms the flat, broad face of the folded absorbent article, while the side width (SW) forms the narrow folded side of the absorbent article.

Figure 5:
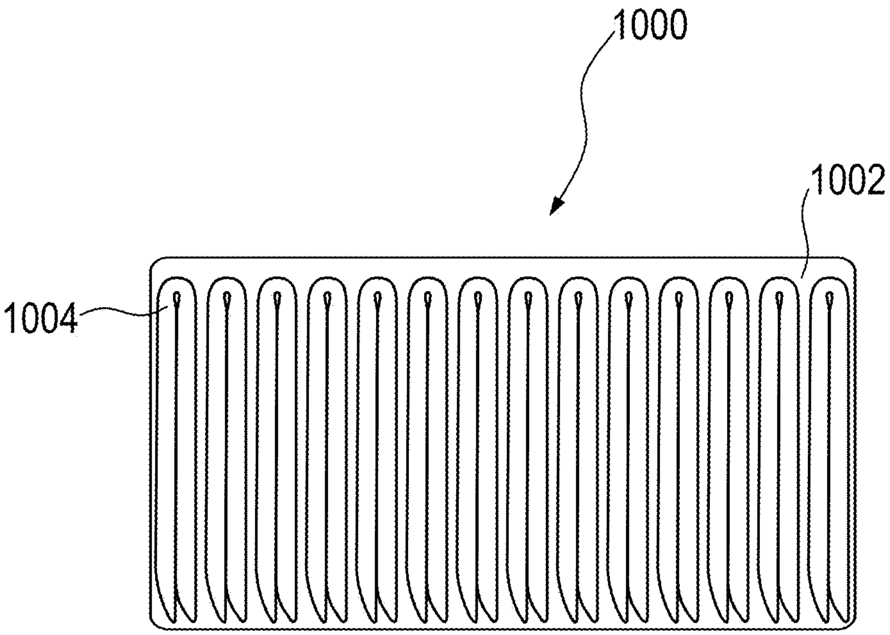
FIG. 5 is a side view of a stack of a plurality of absorbent articles disposed within a package of the present disclosure.
Figure 6:
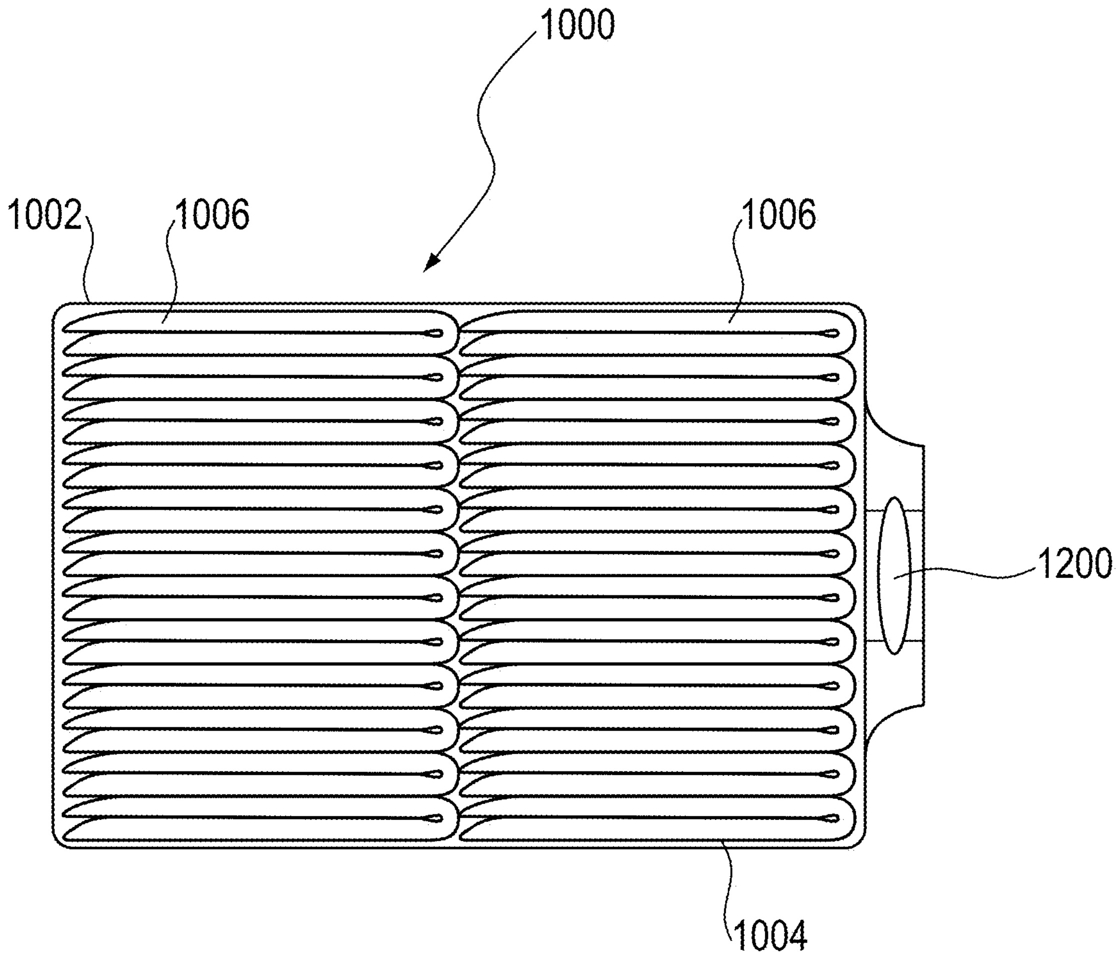
FIG. 6 is a front view of a multiple stacks of a plurality of absorbent articles disposed within a package of the present disclosure.

A plurality of folded articles such as depicted in FIGS. 3B and 4C and 4D may be placed in similar orientation within the interior compartment of a package of the present disclosure. FIGS. 5 and 6 depict a plurality of absorbent articles disposed within a package of the present disclosure. As shown in FIGS. 5 and 6, the package 1000 defines an interior compartment 1002 in which a plurality of absorbent articles 1004 are situated. The plurality of absorbent articles 1004 may be arranged in a single horizontal row, as shown in FIG. 5, or in one or more vertical stacks 1006, as shown in FIG. 6. Where the articles are arranged in more than one vertical stack, as shown in FIG. 6, all the articles may be oriented in the same direction. In another example, a first set of the plurality of folded articles may have their fold noses 30 oriented along one side of the stack, and a second set of the plurality of folded articles may be rotated 180 degrees to have their fold noses oriented along the opposite side of the stack. In some examples, the articles in the first set and the articles in the second set may appear in alternating sequence in the stack.

The folded absorbent articles may be disposed within the package of the present disclosure such that the folded width (FW) faces toward the first and second side panels. Such a configuration may be employed where the number of absorbent articles within the package is relatively large, e.g., greater than about ten individual absorbent articles, because the narrower sides (SW) of the articles will form front and back panels. Therefore, a relatively large number of absorbent articles may then be utilized to build up the front and back panels of the package. Such a configuration may be beneficial where the front and/or back panels form the consumer-facing panel.

The folded absorbent articles may be disposed within the package of the present disclosure such that the folded width (FW) faces toward the front and back panels. Such a configuration may be employed where the number of absorbent articles within the package is relatively low, e.g., less than about ten individual absorbent articles, because the wider sides (FW) of the articles will form front and back panels. Such a configuration may be beneficial where the front and/or back panels form the consumer-facing panel, and the number of absorbent articles disposed within the package is less than about ten.

The absorbent articles or articles may be packed under compression so as to reduce the size of the package, while still providing an adequate number of absorbent articles per package. By packaging the absorbent articles under compression, caregivers can easily handle and store the packages, while also providing distribution savings to manufacturers owing to the reduced size of the packages. Despite lacking the stretch properties of conventional plastic packaging material, the inventors have surprisingly found the package materials of the present disclosure are able to withstand the processing and distribution rigors, as mentioned herein, even with absorbent articles which are compressed within the package and without the use of an intermediate container. This is particularly unexpected as the materials of the present disclosure may not display the stretch properties of presently used conventional plastic films.

Packages of absorbent articles of the present disclosure may have an In-Bag Stack Height of less than about 150 mm, less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 150 mm, from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test Method described herein.

Other Products within the Packages of the Present Disclosure

Many suitable products may be placed within the packages and package materials of the present disclosure, such as consumer products. As an example, packages of the present disclosure may comprise or have contained therein, one or more moisture labile products, humidity labile products, moisture sensitive products, or water vapor sensitive products including unit dose products, unit dose pouches, articles meant for single use, pouches, pouches with fibrous wall materials, pouches with soluble film wall materials, pouches comprising a single layer or ply, and combinations thereof. These unit dose or pouch form products are delivery vehicles comprising active agents or additives designed and intended to provide a benefit to something, such as providing a benefit to an environment external to the unit dose or pouch. The active agents may comprise an active agent containing particle, powder, granule, enscapsulate, and/or pill comprising one or more active agents. Alternatively, the active agents may comprise active an active agent embodied within or located in the cross section of one or more fibers making up the fibrous wall material of the unit dose or pouch.

One embodiment may comprise a unit dose article or pouch where active agents are contained on the internal volume of the unit dose article or pouch. Another embodiment may comprise a unit dose or pouch comprising a single layer or ply where the active agent is contained within the single layer or ply, coated or embedded on the surface of the layer or ply, or a combination of these two configurations. Yet another embodiment may comprise a unit dose or pouch comprising a plurality of plies wherein the active agent is contained within the single layer or ply, coated or embedded on the surface of the layer or ply, between plies or a combination of these configurations.

Active agents may be any suitable additive that produces an intended effect under intended use conditions of the unit dose article or pouch. The active agents may comprise an active agent containing particle or a plurality of particles. For example, the active agent or active agent contained in a particle or particles may be selected from the group consisting of: personal cleansing and/or conditioning agents, such as hair care agents such as shampoo agents and/or hair colorant agents, hair conditioning agents, skin care agents, sunscreen agents, and skin conditioning agents; laundry care and/or conditioning agents such as fabric care agents, fabric conditioning agents, fabric softening agents, fabric anti-wrinkling agents, fabric care anti-static agents, fabric care stain removal agents, soil release agents, dispersing agents, suds suppressing agents, suds boosting agents, anti-foam agents, and fabric refreshing agents; liquid and/or powder dishwashing agents (for hand dishwashing and/or automatic dishwashing machine applications), hard surface care agents, and/or conditioning agents and/or polishing agents; other cleaning and/or conditioning agents such as antimicrobial agents, antibacterial agents, antifungal agents, fabric hueing agents, perfume, bleaching agents (such as oxygen bleaching agents, hydrogen peroxide, percarbonate bleaching agents, perborate bleaching agents, chlorine bleaching agents), bleach activating agents, chelating agents, builders, lotions, brightening agents, air care agents, carpet care agents, dye transfer-inhibiting agents, clay soil removing agents, anti-redeposition agents, polymeric soil release agents, polymeric dispersing agents, alkoxylated polyamine polymers, alkoxylated polycarboxylate polymers, amphilic graft copolymers, dissolution aids, buffering systems, water-softening agents, water-hardening agents, pH adjusting agents, enzymes, flocculating agents, effervescent agents, preservatives, cosmetic agents, make-up removal agents, lathering agents, deposition aid agents, coacervate-forming agents, clays, thickening agents, latexes, silicas, drying agents, odor control agents, antiperspirant agents, cooling agents, warming agents, absorbent gel agents, anti-inflammatory agents, dyes, pigments, acids, and bases; liquid treatment active agents; agricultural active agents; industrial active agents; ingestible active agents such as medicinal agents, teeth whitening agents, tooth care agents, mouthwash agents, periodontal gum care agents, edible agents, dietary agents, vitamins, minerals; water-treatment agents such as water clarifying and/or water disinfecting agents, surfactants, anionic surfactants, cationic surfactants, non-ionic surfactants, zwitterionic surfactants, amphoteric surfactants, one or more silicones, one or more alkali metal or alkaline-earth metal carbonates, alkali metal carbonates (e.g. sodium carbonate, potassium carbonate, etc.), alkali metal hydrogen carbonates (e.g., sodium hydrogen carbonate, potassium hydrogen carbonate, etc.), ammonium carbonate, organic acids (e.g., hydroxy-carboxylic acids [citric acid, tartaric acid, malic acid, lactic acid, gluconic acid, etc.], saturated aliphatic carboxylic acids [acetic acid, succinic acid, etc.], unsaturated aliphatic carboxylic acids [e.g., fumaric acid, etc.], and mixtures thereof.

Example unit dose articles or pouches of the present disclosure include those described in U.S. Pat. Appl. Pub. No. 2013/0172226, U.S. Pat. Appl. Pub. No. 2015/0071572, U.S. Pat. Appl. Pub. No. 2018/0216285, U.S. Pat. Appl. Pub. No. 2018/0216286, U.S. Pat. Appl. Pub. No. 2018/0216287, U.S. Pat. Appl. Pub. No. 2018/0216288, and PCT publications WO 2022/117853, WO 2022/117854, WO 2022/117855, WO 2022/117856, WO 2022/117858, WO 2022/117859, WO 2022/117860, WO 2022/117861.

Test Methods

Tactile Height Test Method

The height and width of a tactile indicium element on the outer surface of a package panel is measured using a 3D Confocal Laser Scanning Microscope (a suitable 3D Confocal Laser Scanning Microscope is the Keyence VK-X1050, commercially available from Keyence Corporation of America, Itasca, IL, USA, or equivalent). The microscope is interfaced with a computer running a measuring, control, and surface texture analysis software (a suitable software is Keyence MultiFileAnalyzer version 2.1.3.89, commercially available from Keyence Corporation of America, Itasca, IL, USA, or equivalent).

The 3D surface Confocal Laser Scanning Microscope measures the surface heights of a sample and produces a map of surface height (z-directional or z-axis) versus displacement in the x-y plane. The surface map is then analyzed by drawing a profile line across the tactile indicium element and measuring the element's height from the base level of the outer surface of the package panel, its width at base level, and its width at half height.

Using a 2.5× objective lens, a 1.0× zoom level, the microscope is programmed to collect a surface height image with a field of view of approximately 5600 microns (μm)× 4200 microns (μm) with an x-y pixel resolution of approximately 5.5 microns (μm)/pixel. If a larger field of view is required, multiple scans, maintaining the x-y resolution, over the surface can be collected and stitched together into a single image for analysis. The height resolution is set at 5 nm/digit, over a sufficient height range to capture all peaks and valleys within the field of view.

Calibrate the instrument according to the manufacturer's specifications.

Place the package panel sample flat on the stage beneath the objective lens with the tactile indicium element facing upward. Collect a surface height image (2-direction) of the sample by following the instrument manufacturer's recommended measurement procedures, which may include using the following settings to minimize noise and maximize the quality of the surface data: Real Peak Detection, single/double scan, surface profile mode, standard area, high-accuracy quality; laser intensity (Brightness and ND filter) set using auto gain. Save the surface height image.

Open the surface height image in the surface texture analysis software. Extract a line profile of the tactile indicium element by drawing a cross-sectional line across the narrowest portion of the element that includes its highest point and extends beyond both sides of the element such that the base level of the sample surface may be identified. This procedure is followed regardless of the element shape (e.g., a dot or line). Identify the base line through the element profile that connects the base level portion of the line profile on either side of the element. Measure the distance from this base level line to the highest point in the element profile and record this value as the height of the tactile indicium to the nearest micron. Measure the width of the element at the base of the element and record this value as the width of the tactile indicium element at the base along the base level line to the nearest micron. At half of the measured height of the tactile indicium element measure the width of the element along a line drawn parallel to the base level line. Record this value as the width of the tactile indicium element at half height to the nearest micron.

This test method can be used to measure either the height of a raised tactile indicium element or the depth of an indented element. To measure the depth of an indented element the cross-sectional line profile is drawn to include the lowest point of the element, and the distance from the base level line to the lowest point is measured. The element width at base level and half depth are performed according to the description above.

Strength Tensile Test Method

The Strength Tensile Test Method is run according to ASTM D828-16 "Standard Test Method for Tensile Properties of Paper and Paperboard Using Constant-Rate-of-Elongation Apparatus" with the following specifications and/or modifications: Two sets of test specimens are cut from package materials containing a weakened region. The first set of test specimens contain the weakened region, such that the weakened region is disposed the entire way across the width test sample and is centered along and perpendicular to the length of the test specimen. The second set of test specimens are cut from the same package materials and are oriented in the same direction as the first set but do not include a weakened region. The specimen length is about 101.6 mm (4 in.) to allow sufficient specimen for clamping in the instrument grips with a distance between the grips of 50.8 mm (2 in.). The rate of grip separation during the test is 300 mm/min. When placing the test specimens containing the weakened region into the grips for testing, the path of the weakened region is to be centered between the grips and perpendicular to the pull axis of the tensile tester. The average tensile strength of the first specimen set containing the weakened region is reported as the Weakened Region Tensile Strength (WRTS) to the nearest 0.01 kN/m. The average tensile strength of the second specimen set without the weakened region is reported as the Package Tensile Strength (MD or CD) to the nearest 0.01 kN/m.

Weakened Region Performance (WRP) Factor—The Weakened Region Performance Factor is calculated by taking the ratio of the Weakened Region Tensile Strength (WRTS) of a package versus the Tensile Strength of the package measured in the same direction (MD or CD). The factor is calculated according to the following equation and reported to the nearest 0.01 units:

$$WRP\text{ Factor} = \frac{\text{Weakened Region Tensile Strength}\left(\frac{\text{kN}}{\text{m}}\right)}{\text{Package Tensile Strength}\left(\frac{\text{kN}}{\text{m}}\right)}$$

Tear Tensile Test Method

The Tear Tensile Test Method is run according to ASTM D2261-13 "Tearing Strength of Fabrics by the Tongue (Single Rip) Procedure (Constant-Rate-of-Extension Tensile Testing Machine), which has been adapted for testing package materials comprising natural materials and a weakened region, with the following specifications and/or modifications: Test specimens are cut from package materials containing a weakened region, such that the path of the weakened region is oriented along the center of the specimen width. The specimen width is 50.4 mm (2 in.), with 25.4 mm (1 in.) on either side of the line of weakened regions. The 75 mm (3 in.) preliminary cut made along the center of the width should not partially cut a land region within the weakened region, such that only whole land regions are torn during the test. A total of five replicate test specimens are prepared. The distance between the clamps is set at 50.4 mm (2 in.) at the start of the test, and a testing speed of 300 mm/min is used. Preconditioning, conditioning, and testing of dry test specimens is performed as specified in ASTM D685-17 "Standard Practice of Conditioning Paper and Paper Products for Testing". Calculation Option 1, Average of Five Highest Peaks, is used to measure the average tear strength (peak force) of each of the first five land areas torn during the test and recorded to the nearest 0.01 N. This procedure is repeated for all five test specimens and the arithmetic mean of the five recorded values is calculated and reported as the Absolute Tear Strength value to the nearest 0.01 N. The Absolute Tear strength value is divided by the average width of all the land areas, which were torn, and peak forces measured during testing, and is reported as the Relative Tear Strength value to the nearest 0.01 N/mm.

Tear Performance Factor (TP Factor)—The Tear Performance Factor is calculated by taking the ratio of the package Weakened Region Tensile Strength (WRTS), according to the Strength Tensile Test Method described herein, versus the Absolute Tear Tensile of the weakened region of the package, according to the Tear Tensile Test Method described herein. The factor is calculated according to the following equation and reported to the nearest 0.01 units:

$$TP\ \text{Factor} = \frac{\text{Weakened Region Tensile Strength}\left(\frac{\text{kN}}{\text{m}}\right)}{\text{Absolute Tear Tensile (N)}}$$

Stretch At Break—Stretch At break is calculated by dividing the Mean Elongation at Break (mm) by the initial test length (test span) of 50.8 mm, and then multiplying by 100. Calculate the stretch at break for the MD replicates and then the CD replicates and report respectively as MD Stretch at Break and CD Stretch at Break to the nearest percent.

Tensile Energy Absorption (TEA)—Tensile Energy Absorption (TEA) is calculated using the following equation:

TEA=(1000*Mean Area Under Curve, mJ)/(width of test sample*initial test length) where the width of the test sample is 25.4 mm, and the initial test length (test span) is 50.8 mm. Calculate the TEA for the MD replicates and then CD replicates and report respectively as MD TEA and CD TEA to the nearest J/$m^2$.

Tensile Energy Absorption (TEA) Index—Tensile Energy Absorption (TEA) Index is calculated using the following equation:

$$TEA\ \text{Index} = (TEA)/\text{Basis Weight}$$

where TEA is in units of J/$m^2$, and Basis Weight is in units of g/$m^2$. Calculate the TEA Index for the MD replicates and then the CD replicates and report respectively as MD TEA Index and CD TEA Index to the nearest J/g.

Burst Strength Test Method

Burst strength is the maximum uniformly distributed pressure that a test sample can withstand. Burst strength is measured in accordance with compendial method ISO 2758 using a test apparatus as described within the method. A suitable instrument is the 13-60 Burst Tester for Paper and Foils available from Testing Machines, Inc (New Castle, DE), or equivalent. The instrument is calibrated and operated as per the manufacturer's instructions. All measurements are performed in a laboratory maintained at 23 °C+/−2 C° and 50%+/−2% relative humidity, and test samples are conditioned in this environment for at least 2 hours prior to testing.

Measurements are made on test samples taken from rolls or sheets of the raw material, or test specimens obtained from a finished package. When excising a test sample from a finished package, use care to not impart any contamination or distortion to the test sample during the process. The test sample must be larger than the clamps used to hold the test sample in the instrument. The test sample should be taken from an area free of folds, wrinkles, or seams.

Measure the burst strength (using a clamping pressure sufficient to prevent slippage during the test, and a pumping rate of 95±15 mL/min) for a total of 10 replicate test samples. For samples that are sided, the side of the test sample that is meant to face the inside of the package faces the pressure when placed into the clamps, and 10 replicates are tested in this orientation. For samples that are balanced (not sided), 5 replicates are tested with the inside of the package facing the pressure and 5 replicates are tested with the outside of the package facing the pressure, and the results are averaged together. Record the pressure at which each test sample bursts to the nearest 0.001 kPa. If the burst pressure is less than 70 kPa, multiple layers of the test material must be used. To obtain the burst strength, divide the burst pressure by the number of layers tested. Calculate the arithmetic mean burst pressure for all replicates and report as Burst Strength to the nearest 0.001 kPa.

Caliper Test Method

The caliper, or thickness, of a single-layer test sample is measured under a static load by a micrometer, in accordance with compendial method ISO 534, with modifications noted herein. All measurements are performed in a laboratory maintained at 23 °C±2 C° and 50%±2% relative humidity and test samples are conditioned in this environment for at least 2 hours prior to testing.

Caliper is measured with a micrometer equipped with a pressure foot capable of exerting a steady pressure of 70 kPa±0.05 kPa onto the test sample. The micrometer is a dead-weight type instrument with readings accurate to 0.1 micron. A suitable instrument is the TMI Digital Micrometer Model 49-56, available from Testing Machines Inc., New Castle, DE, or equivalent. The pressure foot is a flat ground circular movable face with a diameter that is smaller than the test specimen and capable of exerting the required pressure. A suitable pressure foot has a diameter of 16.0 mm. The test sample is supported by a horizontal flat reference platform that is larger than and parallel to the surface of the pressure foot. The system is calibrated and operated per the manufacturer's instructions.

Measurements are made on single-layer test samples taken from rolls or sheets of the raw material, or test samples obtained from a finished package. When excising the test sample from a finished package, use care to not impart any contamination or distortion to the sample during the process.

The excised sample should be free from residual adhesive and taken from an area of the package that is free from any seams or folds. The test sample is ideally 200 $mm^2$ and must be larger than the pressure foot.

To measure caliper, first zero the micrometer against the horizontal flat reference platform. Place the test sample on the platform with the test location centered below the pressure foot. Gently lower the pressure foot with a descent rate of 3.0 mm per second until the full pressure is exerted onto the test sample. Wait 5 seconds and then record the caliper of the test sample to the nearest 0.1 micron. In like fashion, repeat for a total of ten replicate test samples. Calculate the arithmetic mean for all caliper measurements and report the value as Caliper to the nearest 0.1 micron.

Basis Weight Test Method

The basis weight of a test sample is the mass (in grams) per unit area (in square meters) of a single layer of material and is measured in accordance with compendial method ISO 536. The mass of the test sample is cut to a known area, and the mass of the sample is determined using an analytical balance accurate to 0.0001 grams. All measurements are performed in a laboratory maintained at 23 °C±2 C° and 50%±2% relative humidity and test samples are conditioned in this environment for at least 2 hours prior to testing.

Measurements are made on test samples taken from rolls or sheets of the raw material, or test samples obtained from a finished package. When excising the test sample from a finished package, use care to not impart any contamination or distortion to the sample during the process. The excised sample should be free from residual adhesive and taken from an area of the package that is free from any seams or folds. The test sample must be as large as possible so that any inherent material variability is accounted for.

Measure the dimensions of the single layer test sample using a calibrated steel metal ruler traceable to NIST, or equivalent. Calculate the Area of the test sample and record to the nearest 0.0001 square meter. Use an analytical balance to obtain the Mass of the test sample and record to the nearest 0.0001 gram. Calculate Basis Weight by dividing Mass (in grams) by Area (in square meters) and record to the nearest 0.01 grams per square meter (gsm). In like fashion, repeat for a total of ten replicate test samples. Calculate the arithmetic mean for Basis Weight and report to the nearest 0.01 grams/square meter.

In-Bag Stack Height Test Method

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e., each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2 °C and 50±5% relative humidity prior to measurement.

The horizontal sliding plate is raised, and an absorbent article package is placed centrally under the horizontal sliding plate in such a way that the absorbent articles within the package are in a horizontal orientation (see FIG. 6). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured, and the arithmetic mean is reported as the package width. The "In-Bag Stack Height"=(package width/absorbent article count per stack)×10 is calculated and reported to within ±0.5 mm.

Combinations

A1. A package (1) enclosing one or more compressed absorbent articles comprising a plurality of panels forming an outer surface, at least one of the plurality of panels comprises a package material and the package material comprises natural fibers, wherein the outer surface comprises a tactile indicium (2).

A2. The package of paragraph A1, wherein the package (1) is a flexible package.

A3. The package of paragraph A1 or A2, wherein the tactile indicium (2) is an identifier for one or more property of the one or more compressed absorbent articles selected from the group consisting of type, size and absorption capacity.

A4. The package of any one of paragraphs A1 to A3, wherein the tactile indicium (2) comprises braille text according to the 2010 ADA Standards for Accessible Design section 703.3.

A5. The package of any one of paragraphs A1 to A4, wherein the tactile indicium (2) comprises at least one tactile indicium element with a height from 50 μm to 1000 μm, preferably from 100 μm to 950 μm, more preferably from 150 μm to 900 μm, even more preferably from 200 μm to 850 μm or even from 250 μm to 800 μm above the base level according to the Tactile Height Test Method disclosed herein.

A6. The package of any one of paragraphs A1 to A5, wherein the tactile indicium (2) comprises an embossment pattern.

A7. The package of paragraph A6, wherein the embossment pattern is projected outward from the package outer surface.

A8. The package of any one of paragraphs A1 to A7, wherein the plurality of panels forming the outer surface comprise a front panel (14), a back panel (15) opposite the front panel (14), a first side panel (12), a second side panel (13) opposite the first side panel (12), a top panel (11), and a bottom panel (10) opposite the top panel (11), wherein the panels define an interior compartment of the package (1), and wherein one or more compressed absorbent articles are disposed in the interior compartment.

A9. The package of paragraph A8, wherein the front panel (14), the back panel (15), the bottom panel (10), and the top panel (11) are formed of a continuous packaging material.

A10. The package of paragraph A8 or A9, wherein the package (1) comprises one panel in a block bottom, cross bottom, or pinch bottom configuration.

A11. The package of any one of paragraphs A8 to A10, wherein the first side panel (12) comprises a vertical side seam (40) and two angled left side seams (44, 46), and wherein the second side panel (13) comprises a vertical side seam (42) and two angled right side seams (47, 49), wherein a length of the first side panel vertical side seam (40) is greater than a length of the two angled first side panel side seams (44, 46), and wherein a length of the vertical second side panel side seam (42) is greater than a length of the two angled second side panel side seams (47, 49).

A12. The package of any one of paragraphs A1 to A11, wherein the package material is a paper-based material.

A13. The package of any one of paragraphs A1 to A12, wherein the package material comprises a moisture barrier layer.

A14. The package of any one of paragraphs A1 to A13, wherein the package material has a basis weight of between 50 gsm to 120 gsm according to the Basis Weight Test Method disclosed herein.

A15. The package of any one paragraphs A1 to A14, wherein the package material comprises at least 50 percent by weight natural fibers, preferably at least 70 percent by weight natural fibers, more preferably at least 90 percent by weight natural fibers.

A16. The package of any one of paragraphs A1 to A15, wherein the plurality of panels is formed of the package material.

A17. The package of any one of paragraphs A1 to A16, wherein the packaging material has a recyclable percentage of between about 60 percent and about 99.9 percent determined via the PTS-RH:021/97 (Draft October 2019) under category II Test Method disclosed herein.

A18. The package of any one of paragraphs A1 to A17, wherein tactile indicium (2) comprises a brand identifier and/or artwork.

A19. A method of forming a tactile indicium (2) on an outer surface of a package (1) according to any one of paragraphs A1 to A18.

A20. The method of paragraph A19, wherein forming the tactile indicium (2) includes the step of embossing the outer surface.

A21. A bag (4) for forming a package (1) according to any one of paragraphs A1 to A18, wherein the bag comprises a first surface (10), a second surface (12), a third surface (13), a fourth surface (14) and a fifth surface (15), an open end (48) opposing the first surface (10); wherein at least one surface comprises a package material comprising natural fibers; and wherein at least one surface comprises a tactile indicium (2).

A22. The bag according to paragraph A21, wherein the bag (4) comprises wicket-holes (38).

A23. The bag according to paragraph A21, wherein the bag (4) comprises no wicket-holes (38).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A package enclosing one or more compressed absorbent articles, the package comprising a plurality of panels forming an outer surface, at least one of the plurality of panels comprises a package material and the package material comprises natural fibers and has a basis weight of between 50 gsm to 120 gsm according to the Basis Weight Test Method disclosed herein, wherein the outer surface comprises a tactile indicium comprising at least one tactile indicium element with a height from 50 μm to 1000 μm above a base level of the outer surface according to the Tactile Height Test Method disclosed herein, wherein the at least one tactile indicium element is integrally formed of the package material.

2. The package of claim 1, wherein the package is a flexible package.

3. The package of claim 1, wherein the tactile indicium is an identifier for one or more properties of the one or more compressed absorbent articles selected from the group consisting of type, size, and absorption capacity.

4. The package of claim 1, wherein the tactile indicium comprises braille text according to the 2010 ADA Standards for Accessible Design section 703.3.

5. The package of claim 1, wherein the tactile indicium comprises an embossment pattern.

6. The package of claim 5, wherein the embossment pattern is projected outward from the package outer surface.

7. The package of claim 1, wherein the plurality of panels forming the outer surface comprise a front panel, a back panel opposite the front panel, a first side panel, a second side panel opposite the first side panel, a top panel, and a bottom panel opposite the top panel, wherein the panels define an interior compartment of the package, and wherein one or more compressed absorbent articles are disposed in the interior compartment.

8. The package of claim 7, wherein the front panel, the back panel, the bottom panel, and the top panel are formed of a continuous packaging material.

9. The package of claim 7, wherein the package comprises one panel in a block bottom, cross bottom, or pinch bottom configuration.

10. The package of claim 7, wherein the first side panel comprises a vertical side seam and two angled left side seams, and wherein the second side panel comprises a vertical side seam and two angled right side seams, wherein a length of the first side panel vertical side seam is greater than a length of the two angled first side panel side seams, and wherein a length of the vertical second side panel side seam is greater than a length of the two angled second side panel side seams.

11. The package of claim 1, wherein the package material is a paper-based material.

12. The package of claim 1, wherein the package material comprises a moisture barrier layer.

13. The package of claim 1, wherein the package material comprises at least 70 percent by weight natural fibers.

14. The package of claim 1, wherein the plurality of panels is formed of the package material.

15. The package of claim 1, wherein the packaging material has a recyclable percentage of between about 60 percent and about 99.9 percent determined via the PTS-RH: 021/97 (Draft October 2019) under category II Test Method disclosed herein.

16. The package of claim 1, wherein tactile indicium comprises at least one of a brand identifier and artwork.

17. A bag for forming a package of claim 1, wherein the bag comprises a first surface, a second surface, a third surface, a fourth surface and a fifth surface, an open end opposing the first surface; wherein at least one surface of the first surface, the second surface, the third surface, the fourth surface, and the fifth surface comprises a package material comprising natural fibers; and wherein at least one surface comprises a tactile indicium comprising at least one tactile indicium element integrally formed of the package material, the at least one tactile indicium element having a height from 50 μm to 1000 μm above a base level of the at least one surface according to the Tactile Height Test Method disclosed herein.

18. The bag of claim 17, wherein the bag comprises wicket-holes.

19. A package enclosing one or more compressed absorbent articles, the package comprising a plurality of panels forming an outer surface, at least one of the plurality of panels comprises a package material and the package material comprises natural fibers and has a basis weight of between 50 gsm to 120 gsm according to the Basis Weight Test Method disclosed herein, wherein the outer surface comprises a tactile indicium comprising at least one tactile indicium element with a height from 50 μm to 1000 μm above a base level of the outer surface according to the Tactile Height Test Method disclosed herein, wherein the at least one tactile indicium element comprises an embossment of the package material projected outward from the outer surface.

* * * * *